(12) United States Patent
Aragon et al.

(10) Patent No.: US 12,367,954 B1
(45) Date of Patent: *Jul. 22, 2025

(54) METHOD, APPARATUS, AND COMPUTER PROGRAM PRODUCT FOR ESTIMATING A TARGET QUANTITATIVE MEASURE BASED UPON HISTORICAL ELECTRONIC MESSAGES

(71) Applicant: Mckesson Corporation, Irving, TX (US)

(72) Inventors: Stewart Aragon, Hadley, MA (US); Megan Wetzel, Alpharetta, GA (US); Keith Crozier, North Kingstown, RI (US)

(73) Assignee: McKesson Corporation, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/144,426

(22) Filed: Jan. 8, 2021

(51) Int. Cl.
*G06Q 30/02* (2023.01)
*G06Q 30/0207* (2023.01)
*G16H 20/10* (2018.01)

(52) U.S. Cl.
CPC ......... *G16H 20/10* (2018.01); *G06Q 30/0207* (2013.01)

(58) Field of Classification Search
CPC ..... G16H 20/10; G06Q 30/0207; H04L 67/10
See application file for complete search history.

(56) References Cited

U.S. PATENT DOCUMENTS

| | | |
|---|---|---|
| 5,012,035 A | 4/1991 | Sartori et al. |
| 5,173,851 A | 12/1992 | Off et al. |
| 5,595,342 A | 1/1997 | McNair et al. |
| 5,628,530 A | 5/1997 | Thornton |
| 5,726,092 A | 3/1998 | Mathews et al. |
| 5,757,898 A | 5/1998 | Nishikawa |
| 5,769,228 A | 6/1998 | Wroblewski |

(Continued)

FOREIGN PATENT DOCUMENTS

| | | |
|---|---|---|
| AU | 2003243327 A | 12/2003 |
| CA | 2 482 370 A1 | 3/2006 |

(Continued)

OTHER PUBLICATIONS

University of Chicago, Chris Hsee, "General Evaluability Theory" vol. 5 No. 4 of Perspectives on Psychological Science, pp. 343-355 (Year: 2010).*

(Continued)

*Primary Examiner* — Breffni Baggot
(74) *Attorney, Agent, or Firm* — Alston & Bird LLP

(57) ABSTRACT

A method, apparatus and computer program product are provided to estimate at least one target quantitative measure based upon historical electronic messages. The historical electronic messages may be partitioned based on geographic areas. The target quantitative measure may be estimated based upon respective binary categorical indicators, and respective quantitative measures of the historical electronic messages. The target quantitative measure may be adjusted dependent upon a quantitative criterion of an entity. The target quantitative measure may be used to price prescription drugs and/or the like, and may impact prescription adherence and/or pharmacy profit margins.

8 Claims, 3 Drawing Sheets

(56) References Cited

U.S. PATENT DOCUMENTS

| | | | |
|---|---|---|---|
| 6,012,035 A | 1/2000 | Freeman et al. | |
| 6,111,218 A | 8/2000 | Akers et al. | |
| 6,463,462 B1 | 10/2002 | Smith et al. | |
| 6,595,342 B1 | 7/2003 | Maritzen et al. | |
| 6,726,092 B2 | 4/2004 | Goldberg et al. | |
| 6,757,898 B1 | 6/2004 | Ilsen et al. | |
| 6,769,228 B1 | 8/2004 | Mahar | |
| 7,155,397 B2 | 12/2006 | Alexander et al. | |
| 7,192,741 B2 | 3/2007 | Otte et al. | |
| 7,337,129 B1 | 2/2008 | Lowry et al. | |
| 7,346,768 B2 | 3/2008 | DiRienzo | |
| 7,409,632 B1 | 8/2008 | DiRienzo | |
| 7,426,476 B2 | 9/2008 | Munoz et al. | |
| 7,734,483 B1 | 6/2010 | Smith et al. | |
| 7,783,383 B2 | 8/2010 | Eliuk et al. | |
| 7,840,424 B2 | 11/2010 | Wiley et al. | |
| 7,856,364 B1 | 12/2010 | Wiley et al. | |
| 7,912,741 B1 | 3/2011 | Pinsonneault | |
| 7,921,021 B1 | 4/2011 | Newman | |
| 8,036,913 B1 | 10/2011 | Pinsonneault et al. | |
| 8,036,914 B1 | 10/2011 | Pinsonneault | |
| 8,036,918 B1 | 10/2011 | Pinsonneault | |
| 8,050,943 B1 | 11/2011 | Wiley et al. | |
| 8,060,379 B1 | 11/2011 | Pinsonneault et al. | |
| 8,126,743 B1 | 2/2012 | Wilk | |
| 8,326,773 B1 | 12/2012 | Bellamy | |
| 8,346,571 B2 | 1/2013 | Kalies, Jr. | |
| 8,412,537 B1 | 4/2013 | Fenton et al. | |
| 8,442,847 B1 | 5/2013 | Shrivastava | |
| 8,489,415 B1 | 7/2013 | Ringold | |
| 8,521,557 B1 | 8/2013 | Ringold et al. | |
| 8,560,340 B1 | 10/2013 | Ringold | |
| 8,639,523 B1 | 1/2014 | Pinsonneault | |
| 8,645,162 B2 | 2/2014 | Boerger et al. | |
| 8,671,018 B2 | 3/2014 | Thomas et al. | |
| 8,712,797 B1 | 4/2014 | Bezdek et al. | |
| 8,738,399 B1 | 5/2014 | Abou Nader et al. | |
| 8,786,650 B1 * | 7/2014 | Eller .................. | B41J 3/4073 705/2 |
| 8,799,018 B1 | 8/2014 | Rea et al. | |
| 8,984,059 B2 | 3/2015 | Johnson | |
| 9,026,507 B2 | 5/2015 | Shraim et al. | |
| 9,100,793 B2 | 8/2015 | Johnson | |
| 9,171,322 B2 | 10/2015 | Spievak et al. | |
| 9,356,947 B2 | 5/2016 | Shraim et al. | |
| 9,760,871 B1 | 9/2017 | Pourfallah et al. | |
| 9,779,129 B1 | 10/2017 | Lequeux | |
| 9,786,023 B2 | 10/2017 | Cohan et al. | |
| 10,109,027 B1 | 10/2018 | Stack | |
| 10,157,262 B1 | 12/2018 | Pinsonneault | |
| 10,331,855 B1 | 6/2019 | Bratton et al. | |
| 10,417,380 B1 | 9/2019 | Kaye et al. | |
| 10,489,552 B2 | 11/2019 | Pinsonneault | |
| 10,496,793 B1 | 12/2019 | Lawrence et al. | |
| 10,565,656 B1 | 2/2020 | Pinsonneault et al. | |
| 10,606,984 B1 | 3/2020 | Kaye et al. | |
| 10,616,146 B1 | 4/2020 | Hopkins et al. | |
| 10,628,797 B2 | 4/2020 | Shraim et al. | |
| 10,642,812 B1 | 5/2020 | Hopkins et al. | |
| 10,713,694 B1 | 7/2020 | Harris et al. | |
| 10,747,848 B2 | 8/2020 | Guinan | |
| 10,778,618 B2 | 9/2020 | Karnin et al. | |
| 10,862,832 B1 | 12/2020 | Harris | |
| 10,924,545 B2 | 2/2021 | Momchilov et al. | |
| 10,924,585 B1 | 2/2021 | Harris et al. | |
| 10,929,932 B1 | 2/2021 | Golden et al. | |
| 10,978,198 B1 | 4/2021 | Pinsonneault | |
| 10,999,224 B1 | 5/2021 | Frechen et al. | |
| 11,043,293 B1 | 6/2021 | Salzbrenner | |
| 11,170,394 B1 | 11/2021 | Macinski | |
| 11,443,835 B1 | 9/2022 | Gangaikondan-Iyer et al. | |
| 11,508,471 B1 | 11/2022 | Anselmi et al. | |
| 11,640,618 B1 | 5/2023 | Burdine | |
| 2001/0029483 A1 | 10/2001 | Schultz et al. | |
| 2001/0037216 A1 | 11/2001 | Oscar et al. | |
| 2001/0039589 A1 | 11/2001 | Aho et al. | |
| 2001/0056359 A1 | 12/2001 | Abreu | |
| 2002/0002495 A1 | 1/2002 | Ullman | |
| 2002/0004812 A1 | 1/2002 | Motoyama | |
| 2002/0032582 A1 | 3/2002 | Feeney et al. | |
| 2002/0032583 A1 | 3/2002 | Joao | |
| 2002/0035484 A1 | 3/2002 | McCormick | |
| 2002/0087583 A1 | 7/2002 | Morgan et al. | |
| 2002/0111832 A1 | 8/2002 | Judge | |
| 2002/0133379 A1 | 9/2002 | Lewis et al. | |
| 2002/0143579 A1 | 10/2002 | Docherty et al. | |
| 2002/0147614 A1 | 10/2002 | Doerr et al. | |
| 2002/0188552 A1 | 12/2002 | Kavounas et al. | |
| 2002/0198831 A1 | 12/2002 | Patricelli et al. | |
| 2003/0009367 A1 | 1/2003 | Morrison | |
| 2003/0050796 A1 | 3/2003 | Baldwin | |
| 2003/0050799 A1 | 3/2003 | Jay et al. | |
| 2003/0069760 A1 | 4/2003 | Gelber | |
| 2003/0074234 A1 | 4/2003 | Stasny | |
| 2003/0097310 A1 | 5/2003 | Ono et al. | |
| 2003/0130875 A1 | 7/2003 | Hawash et al. | |
| 2003/0149625 A1 | 8/2003 | Leonardi et al. | |
| 2003/0154163 A1 | 8/2003 | Phillips et al. | |
| 2003/0172008 A1 | 9/2003 | Hage et al. | |
| 2003/0187690 A1 | 10/2003 | Miller | |
| 2003/0229540 A1 | 12/2003 | Algiene | |
| 2003/0236747 A1 | 12/2003 | Sager | |
| 2004/0006490 A1 | 1/2004 | Gingrich et al. | |
| 2004/0039599 A1 | 2/2004 | Fralic | |
| 2004/0054685 A1 | 3/2004 | Rahn et al. | |
| 2004/0059607 A1 | 3/2004 | Ball et al. | |
| 2004/0073456 A1 | 4/2004 | Gottlieb et al. | |
| 2004/0073457 A1 | 4/2004 | Kalies | |
| 2004/0078222 A1 | 4/2004 | Khan et al. | |
| 2004/0078234 A1 | 4/2004 | Tallal, Jr. | |
| 2004/0088187 A1 | 5/2004 | Chudy et al. | |
| 2004/0103062 A1 | 5/2004 | Wood et al. | |
| 2004/0117323 A1 | 6/2004 | Mindala | |
| 2004/0148198 A1 | 7/2004 | Kalies | |
| 2004/0153336 A1 | 8/2004 | Virdee et al. | |
| 2004/0199545 A1 | 10/2004 | Wagner et al. | |
| 2004/0236630 A1 | 11/2004 | Kost et al. | |
| 2004/0249745 A1 | 12/2004 | Baaren | |
| 2005/0015280 A1 | 1/2005 | Gabel et al. | |
| 2005/0060201 A1 | 3/2005 | Connely, III et al. | |
| 2005/0065821 A1 | 3/2005 | Kalies, Jr. | |
| 2005/0075932 A1 | 4/2005 | Mankoff | |
| 2005/0080692 A1 | 4/2005 | Padam et al. | |
| 2005/0102169 A1 | 5/2005 | Wilson | |
| 2005/0154627 A1 | 7/2005 | Zuzek et al. | |
| 2005/0187793 A1 | 8/2005 | Myles | |
| 2005/0197862 A1 | 9/2005 | Paterson et al. | |
| 2005/0240442 A1 | 10/2005 | Lapsker et al. | |
| 2005/0240473 A1 | 10/2005 | Ayers, Jr. et al. | |
| 2005/0261939 A1 | 11/2005 | Augspurger et al. | |
| 2005/0288972 A1 | 12/2005 | Marvin et al. | |
| 2006/0020514 A1 | 1/2006 | Yered | |
| 2006/0026041 A1 | 2/2006 | Ullman | |
| 2006/0036470 A1 | 2/2006 | Oaks | |
| 2006/0085231 A1 | 4/2006 | Brofman | |
| 2006/0085385 A1 | 4/2006 | Foster et al. | |
| 2006/0113376 A1 | 6/2006 | Reed et al. | |
| 2006/0149595 A1 | 7/2006 | Williams et al. | |
| 2006/0149784 A1 | 7/2006 | Tholl et al. | |
| 2006/0184391 A1 | 8/2006 | Barre et al. | |
| 2006/0212318 A1 | 9/2006 | Dooley | |
| 2006/0212345 A1 | 9/2006 | Soza et al. | |
| 2006/0224414 A1 | 10/2006 | Astrup et al. | |
| 2006/0224417 A1 | 10/2006 | Werner | |
| 2006/0224443 A1 | 10/2006 | Soza et al. | |
| 2006/0235747 A1 | 10/2006 | Hammond et al. | |
| 2006/0259363 A1 | 11/2006 | Jhetam et al. | |
| 2007/0005402 A1 | 1/2007 | Kennedy et al. | |
| 2007/0033137 A1 | 2/2007 | Provost et al. | |
| 2007/0043589 A1 | 2/2007 | Warren et al. | |
| 2007/0043595 A1 | 2/2007 | Pederson | |
| 2007/0050209 A1 | 3/2007 | Yered | |
| 2007/0050210 A1 | 3/2007 | Wiley, II | |
| 2007/0067186 A1 | 3/2007 | Brenner et al. | |

(56) References Cited

U.S. PATENT DOCUMENTS

| | | |
|---|---|---|
| 2007/0094133 A1 | 4/2007 | Anandarao et al. |
| 2007/0108053 A1 | 5/2007 | Cramer et al. |
| 2007/0136100 A1 | 6/2007 | Daugherty et al. |
| 2007/0162303 A1 | 7/2007 | Wiley et al. |
| 2007/0168228 A1 | 7/2007 | Lawless |
| 2007/0185799 A1 | 8/2007 | Harrison et al. |
| 2007/0191985 A1 | 8/2007 | Bain |
| 2007/0194352 A1 | 8/2007 | Han |
| 2007/0202886 A1 | 8/2007 | Dhebri et al. |
| 2007/0204043 A1 | 8/2007 | Espinosa et al. |
| 2007/0219813 A1 | 9/2007 | Moore |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2007/0250341 A1 | 10/2007 | Howe et al. |
| 2007/0260750 A1 | 11/2007 | Feied et al. |
| 2007/0276697 A1 | 11/2007 | Wiley et al. |
| 2007/0294765 A1 | 12/2007 | Rihn et al. |
| 2007/0299915 A1 | 12/2007 | Shraim et al. |
| 2008/0033750 A1 | 2/2008 | Swiss et al. |
| 2008/0103836 A1 | 5/2008 | Park et al. |
| 2008/0112411 A1 | 5/2008 | Stafford et al. |
| 2008/0152107 A1 | 6/2008 | Mendiola |
| 2008/0183492 A1 | 7/2008 | Warren et al. |
| 2008/0215361 A1 | 9/2008 | Nunnari et al. |
| 2008/0262948 A1 | 10/2008 | Grady et al. |
| 2009/0006141 A1 | 1/2009 | Karr |
| 2009/0030719 A1 | 1/2009 | Nadas et al. |
| 2009/0064330 A1 | 3/2009 | Shraim et al. |
| 2009/0083064 A1 | 3/2009 | Mahinda |
| 2009/0094051 A1 | 4/2009 | Ard et al. |
| 2009/0100099 A1 | 4/2009 | Buckwalter |
| 2009/0106313 A1 | 4/2009 | Boldyga |
| 2009/0112707 A1 | 4/2009 | Weiss et al. |
| 2009/0198510 A1 | 8/2009 | Ditto |
| 2009/0204477 A1 | 8/2009 | Urso |
| 2009/0287558 A1 | 11/2009 | Seth et al. |
| 2009/0313112 A1 | 12/2009 | Champ et al. |
| 2009/0327363 A1 | 12/2009 | Cullen et al. |
| 2010/0030667 A1 | 2/2010 | Chudy et al. |
| 2010/0070298 A1 | 3/2010 | Kalies |
| 2010/0144259 A1 | 6/2010 | Allexon et al. |
| 2010/0145730 A1 | 6/2010 | Abreu |
| 2010/0161353 A1 | 6/2010 | Mayaud |
| 2010/0217622 A1 | 8/2010 | Brown et al. |
| 2010/0285821 A1 | 11/2010 | Smeeding et al. |
| 2010/0287001 A1 | 11/2010 | Pearce et al. |
| 2010/0293236 A1 | 11/2010 | Wisner et al. |
| 2011/0015978 A1 | 1/2011 | Welch, Jr. |
| 2011/0112871 A1 | 5/2011 | Simonowski et al. |
| 2011/0161109 A1 | 6/2011 | Pinsonneault et al. |
| 2011/0196697 A1 | 8/2011 | Akers |
| 2011/0288925 A1 | 11/2011 | Thomas et al. |
| 2012/0053958 A1* | 3/2012 | Marshall ............... G06Q 30/02 705/2 |
| 2012/0109839 A1 | 5/2012 | Anderson et al. |
| 2012/0136809 A1 | 5/2012 | Cannata et al. |
| 2012/0143627 A1 | 6/2012 | Ruben et al. |
| 2012/0166268 A1 | 6/2012 | Griffiths |
| 2012/0179481 A1* | 7/2012 | Patel ..................... G06Q 30/02 705/2 |
| 2012/0185263 A1 | 7/2012 | Emert |
| 2012/0185264 A1 | 7/2012 | Demogenes et al. |
| 2012/0253829 A1 | 10/2012 | John et al. |
| 2012/0253830 A1 | 10/2012 | John et al. |
| 2012/0253831 A1 | 10/2012 | John et al. |
| 2012/0253832 A1 | 10/2012 | John et al. |
| 2012/0253833 A1 | 10/2012 | John et al. |
| 2012/0253846 A1 | 10/2012 | John et al. |
| 2012/0265591 A1 | 10/2012 | Hwang |
| 2012/0323608 A1 | 12/2012 | Herzlinger |
| 2013/0041968 A1 | 2/2013 | Cohen et al. |
| 2013/0046610 A1 | 2/2013 | Abraham |
| 2013/0103602 A1 | 4/2013 | Melnick et al. |
| 2013/0144715 A1 | 6/2013 | Kranzley et al. |
| 2013/0179180 A1 | 7/2013 | Patra |
| 2013/0191147 A1 | 7/2013 | Harrell |
| 2013/0197980 A1 | 8/2013 | Lerner et al. |
| 2013/0246082 A1 | 9/2013 | Brylawski et al. |
| 2013/0311389 A1 | 11/2013 | Kaehler et al. |
| 2014/0039911 A1 | 2/2014 | Iyer |
| 2014/0088985 A1 | 3/2014 | Grant et al. |
| 2014/0214435 A1 | 7/2014 | Previdi |
| 2014/0249861 A1 | 9/2014 | Gamble et al. |
| 2014/0249864 A1 | 9/2014 | Sultan et al. |
| 2014/0278448 A1 | 9/2014 | Sadeghi et al. |
| 2014/0278456 A1 | 9/2014 | Milosevich et al. |
| 2014/0278531 A1 | 9/2014 | Gupta |
| 2015/0032465 A1 | 1/2015 | Sundar et al. |
| 2015/0088557 A1 | 3/2015 | Huynh et al. |
| 2015/0142479 A1 | 5/2015 | Porter et al. |
| 2015/0149197 A1 | 5/2015 | Guinan |
| 2015/0154565 A1 | 6/2015 | Kaehler et al. |
| 2015/0154588 A1 | 6/2015 | Purves et al. |
| 2015/0195224 A1 | 7/2015 | Karnin et al. |
| 2015/0213195 A1 | 7/2015 | Blechman |
| 2015/0234991 A1 | 8/2015 | Pinsonneault |
| 2015/0235177 A1 | 8/2015 | Shraim et al. |
| 2015/0269695 A1 | 9/2015 | Pinsonneault et al. |
| 2015/0278472 A1 | 10/2015 | King |
| 2015/0332422 A1 | 11/2015 | Gilmartin |
| 2015/0371000 A1 | 12/2015 | Pinsonneault |
| 2016/0012465 A1 | 1/2016 | Sharp |
| 2016/0103978 A1 | 4/2016 | Stong |
| 2016/0140593 A1 | 5/2016 | Smeeding et al. |
| 2016/0213512 A1 | 7/2016 | Palanker et al. |
| 2016/0267544 A1 | 9/2016 | Flood et al. |
| 2016/0267545 A1 | 9/2016 | Glass et al. |
| 2016/0307195 A1 | 10/2016 | Cantwell et al. |
| 2016/0321406 A1 | 11/2016 | Timmerman et al. |
| 2016/0321410 A1 | 11/2016 | Timmerman et al. |
| 2016/0358142 A1 | 12/2016 | Hillen |
| 2016/0358293 A1 | 12/2016 | Berger et al. |
| 2016/0359795 A1 | 12/2016 | Fehling |
| 2017/0034087 A1 | 2/2017 | Borenstein et al. |
| 2017/0039331 A1 | 2/2017 | Bezdek et al. |
| 2017/0220768 A1 | 8/2017 | Tanner, Jr. et al. |
| 2017/0255759 A1 | 9/2017 | McGrath |
| 2017/0323295 A1 | 11/2017 | Kranzley et al. |
| 2017/0324695 A1 | 11/2017 | Fischer et al. |
| 2017/0329922 A1 | 11/2017 | Eberting et al. |
| 2018/0012244 A1 | 1/2018 | Leonardi |
| 2018/0075212 A1 | 3/2018 | Kubey |
| 2018/0075215 A1 | 3/2018 | Loiacoono |
| 2018/0366810 A1 | 12/2018 | Nero et al. |
| 2019/0095582 A1 | 3/2019 | Waits |
| 2019/0213212 A1 | 7/2019 | Adato et al. |
| 2019/0252049 A1 | 8/2019 | Fotsch et al. |
| 2019/0385733 A1 | 12/2019 | Kaye et al. |
| 2019/0385734 A1 | 12/2019 | Pinsonneault |
| 2020/0105392 A1 | 4/2020 | Karkazis et al. |
| 2020/0372988 A1 | 11/2020 | Bezdek et al. |
| 2021/0319887 A1* | 10/2021 | Derrick, Jr. ........... A61B 5/7275 |
| 2021/0374872 A1 | 12/2021 | Stewart et al. |
| 2021/0374876 A1 | 12/2021 | Cedergreen |

FOREIGN PATENT DOCUMENTS

| | | |
|---|---|---|
| CA | 2792252 A1 | 4/2013 |
| CA | 2810686 A1 | 10/2013 |
| CN | 102362778 | 2/2012 |
| KR | 100755440 | 9/2007 |
| KR | 100793852 | 1/2008 |
| KR | 101038074 | 6/2011 |
| KR | 101101692 | 12/2011 |
| KR | 20110138108 | 12/2011 |
| KR | 20110138572 | 12/2011 |
| KR | 101154858 | 6/2012 |
| WO | WO 1991/006917 A1 | 5/1991 |
| WO | WO 1995/003569 A2 | 2/1995 |
| WO | WO 1997/025682 A1 | 7/1997 |
| WO | WO 1998/050871 A1 | 11/1998 |
| WO | WO 2000/039737 A1 | 7/2000 |
| WO | WO 2003/098401 A2 | 11/2003 |

(56) References Cited

FOREIGN PATENT DOCUMENTS

| WO | WO 2007/025295 A2 | 3/2007 |
|---|---|---|
| WO | WO 2007/094772 A1 | 8/2007 |
| WO | WO 2008/092109 A2 | 7/2008 |

OTHER PUBLICATIONS

University of Chicago, "Nature of the Firm", Economica vol. 4 No. 16 pp. 386-405 by Nobel Prize Winner Ron Coase (Year: 1937).*
United States Patent and Trademark Office, Notice of Allowance received for U.S. Appl. No. 16/043,401, dated Aug. 10, 2020, 9 pages, U.S.A.
U.S. Appl. No. 16/792,413, "Method, Apparatus and Computer Program Product for Partitioning Prescription Transaction Costs in an Electronic Prescription Transaction," Unpublished (filed Feb. 17, 2020), (Jared Burdine, Inventor) (McKesson Corporation, Assignee).
U.S. Appl. No. 16/867,286, "Method, Apparatus, and Computer Program Product for Constructing Electronic Message Responses Dependent Upon Historical Information," Unpublished (filed May 5, 2020), (Jared Burdine, et al., Inventor) (McKesson Corporation, Assignee).
U.S. Appl. No. 17/012,565, "Method, Apparatus, and Computer Program Product for Performing an Alternative Evaluation Procedure in Response to an Electronic Message," Unpublished (filed Sep. 4, 2020), (Stacy Hopkins, et al., Inventors) (McKesson Corporation, Assignee).
U.S. Appl. No. 17/092,705, "Computing System and Method for Automatically Reversing an Action Indicated by an Electronic Message," Unpublished (filed Nov. 9, 2020), (Patrick Harris, Inventor) (McKesson Corporation, Assignee).
United States Patent and Trademark Office, Notice of Allowance received for U.S. Appl. No. 17/092,705, dated Dec. 23, 2021, 42 pages, U.S.
United States Patent and Trademark Office, Non-Final Office Action received for U.S. Appl. No. 15/085,166, dated Jan. 10, 2022, 12 pages, U.S.
United States Patent and Trademark Office, Final Office Action received for U.S. Appl. No. 16/792,413, dated Jan. 10, 2022, 80 pages, U.S.
United States Patent and Trademark Office, Advisory Action received for U.S. Appl. No. 16/832,318, dated Jan. 28, 2022, 4 pages, U.S.
United States Patent and Trademark Office, Non-Final Office Action received for U.S. Appl. No. 16/867,286, dated Feb. 22, 2022, 38 pages, U.S.
United States Patent and Trademark Office, Notice of Allowance received for U.S. Appl. No. 17/219,526, dated Feb. 3, 2022, 48 pages, U.S.
Zhu, V. et al., "Data for drugs available through low-cost prescription drug programs are available through pharmacy benefit manager and claims data," BMC Clinical Pharmacology, Jun. 22, 2012, vol. 12, No. 12., BioMed Central Ltd., UK.
United States Patent and Trademark Office, Notice of Allowance received for U.S. Appl. No. 15/085,166, dated Sep. 10, 2021, 21 pages, U.S.
United States Patent and Trademark Office, Corrected Notice of Allowability received for U.S. Appl. No. 15/085,166, dated Sep. 20, 2021, 6 pages, U.S.
United States Patent and Trademark Office, Non-Final Office Action received for U.S. Appl. No. 17/012,565, dated Apr. 12, 2022, 19 pages, U.S.A.
United States Patent and Trademark Office, Non-Final Office Action received for U.S. Appl. No. 16/453,509, dated Apr. 28, 2022, 16 pages, U.S.A.
United States Patent and Trademark Office, Non-Final Office Action received for U.S. Appl. No. 16/552,021, dated May 3, 2022, 60 pages, U.S.A.
United States Patent and Trademark Office, Non-Final Office Action received for U.S. Appl. No. 17/175,939, dated May 12, 2022, 48 pages, U.S.A.

Pharmacy Reject Codes NCPDP, 5 pages.
St. Vincent's first to use Birmingham startup's information system. The Birmingham News [Online] Apr. 11, 2005. URL: http://www.awarix.com.
St. Vincent's is Digital Flagship D. Lockridge; Birmingham Medical News [Online] Sep. 2005.
Two automatic identification technology, neither new in the sense if being recent developments . . . Patient Safety & Quality Healthcare [Online] Aug. 2005_ URL: http://www_awarix.com.
Advisory Action for U.S. Appl. No. 14/193,294 mailed Nov. 9, 2017, 3 pages.
Advisory Action for U.S. Appl. No. 15/085,166 dated Apr. 11, 2019, 4 pages.
Advisory Action for U.S. Appl. No. 15/085,166 dated Apr. 29, 2020, 3 pages.
Advisory Action for U.S. Appl. No. 15/137,371 mailed Feb. 25, 2019, 5 pages.
Advisory Action for U.S. Appl. No. 15/427,746 mailed Jul. 2, 2019, 2 pages.
Advisory Action received for U.S. Appl. No. 15/085,166, dated Jan. 29, 2021, 3 pages, US.
Almaro, Moshe; "Recovery and Reuse of Unused Prescription Drugs" MIT What Matters: Aug. 2005.
American Society of Health-System Pharmacists (ASHP), "Is Prescribing the Next Step in the Evolution of Pharmacy?" May 15, 2012.
Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.
Anonymous, Medic; On-line Goes In-House, Chain Store Age Executive, Jan. 1987, vol. 63, Issue 1, USA; Abstract only.
Anonymous, Pharmacy Industry Leaders Launch Firm to Supply Real-Time Data, PR Newswire, Jul. 30, 2001, p. 1, New York, NY, USA.
Anonymous, TechRx Announces Successful Beta Deployment of T-Rex. PR Newswire. May 13, 2002.
Consalvo, Bob; "City of Boston in the City Council" hearing notice, Dec. 6, 2006.
Coping with Information Overload. The News Source for Healthcare Information Technology [Online] Nov. 2004. URL: http://www.awarix.com.
Decision to Grant European Patent Application No. 13809457.8 dated May 18, 2017.
Examiner's Answer for U.S. Appl. No. 14/145,027 mailed Sep. 7, 2016, 27 pages.
Extended European Search Report for European Application No. 13809457.8 dated Apr. 15, 2016, 6 pages.
Final Office Action for U.S. Appl. No. 12/140,015 mailed Jan. 31, 2011, 10 pages.
Final Office Action for U.S. Appl. No. 12/415,062 mailed Oct. 6, 2011, 18 pages.
Final Office Action for U.S. Appl. No. 12/555,589 mailed Apr. 11, 2012, 17 pages.
Final Office Action for U.S. Appl. No. 12/560,071 mailed Aug. 28, 2015, 8 pages.
Final Office Action for U.S. Appl. No. 12/560,071 mailed Nov. 8, 2012, 11 pages.
Final Office Action for U.S. Appl. No. 12/570,982 mailed Apr. 11, 2014, 22 pages.
Final Office Action for U.S. Appl. No. 12/570,982 mailed Aug. 28, 2015, 10 pages.
Final Office Action for U.S. Appl. No. 12/570,982 mailed Jan. 17, 2013, 19 pages.
Final Office Action for U.S. Appl. No. 12/730,015 mailed Aug. 14, 2012, 10 pages.
Final Office Action for U.S. Appl. No. 12/978,898 mailed May 16, 2013, 16 pages.
Final Office Action for U.S. Appl. No. 13/721,890 mailed Jun. 24, 2015, 14 pages.
Final Office Action for U.S. Appl. No. 13/721,890 mailed Nov. 25, 2016, 12 pages.

(56) References Cited

OTHER PUBLICATIONS

Final Office Action for U.S. Appl. No. 13/782,909 mailed May 31, 2016, 18 pages.
Final Office Action for U.S. Appl. No. 13/782,909 mailed Oct. 6, 2015, 24 pages.
Final Office Action for U.S. Appl. No. 13/804,175 mailed Oct. 6, 2015, 6 pages.
Final Office Action for U.S. Appl. No. 13/827,676 mailed Jul. 13, 2015, 17 pages.
Final Office Action for U.S. Appl. No. 14/090,113 mailed Jan. 6, 2016, 18 pages.
Final Office Action for U.S. Appl. No. 14/090,122 mailed Apr. 22, 2016, 13 pages.
Final Office Action for U.S. Appl. No. 14/145,027 mailed Nov. 19, 2015, 12 pages.
Final Office Action for U.S. Appl. No. 14/193,294 mailed May 2, 2016, 29 pages.
Final Office Action for U.S. Appl. No. 14/218,326 mailed Jun. 30, 2016, 17 pages.
Final Office Action for U.S. Appl. No. 15/085,166, dated Dec. 4, 2020, 11 pages.
Final Office Action for U.S. Appl. No. 15/137,371 mailed Nov. 28, 2018, 24 pages.
Final Office Action for U.S. Appl. No. 15/427,746 mailed Apr. 15, 2019, 9 pages.
Kaplan et al., "Let the Needles Do the Talking! Evaluating the New Haven Needle Exchange." Interfaces 23:1, Jan.-Feb. 1993 (pp. 7-26).
Lamb, J., New Era of Electronic Medicine Management: E-Prescriptions, Britain's Traditionally Cautious National Health Service is Starting Trials for Online Prescription, with the Aim of Cutting Costs, Finance Times, London, Feb. 21, 2001, p. 6, London, United Kingdom.
Letter Restarting Period for Response for U.S. Appl. No. 13/721,890 mailed Jan. 14, 2015, 11 pages.
Marie Chisholm et al. "Pharmaceutical Manufacturer Assistance Program." Arch Intern Med. vol. 162, Apr. 8, 2002.
Non-Final Office Action for U.S. Appl. No. 12/560,071 mailed Jun. 21, 2012, 11 pages.
Non-Final Office Action for U.S. Appl. No. 12/570,982 mailed Jun. 20, 2012, 10 pages.
Non-Final Office Action for U.S. Appl. No. 14/193,294 mailed Feb. 21, 2017, 32 pages.
Non-Final Office Action for U.S. Appl. No. 15/085,166 dated Jun. 12, 2020, 26 pages.
Non-Final Office Action for U.S. Appl. No. 16/180,915 dated Jun. 1, 2020, 40 pages.
Non-final Office Action for U.S. Appl. No. 12/140,015 mailed Oct. 8, 2010, 9 pages.
Non-final Office Action for U.S. Appl. No. 12/189,650 mailed Jan. 22, 2010, 11 pages.
Non-final Office Action for U.S. Appl. No. 12/189,654 mailed Jan. 22, 2010, 11 pages.
Non-Final Office Action for U.S. Appl. No. 12/388,956 mailed Feb. 3, 2011, 11 pages.
Non-Final Office Action for U.S. Appl. No. 12/415,062 mailed Mar. 30, 2011, 23 pages.
Non-Final Office Action for U.S. Appl. No. 12/555,589 mailed Dec. 9, 2011, 12 pages.
Non-Final Office Action for U.S. Appl. No. 12/560,071 mailed Sep. 23, 2014, 17 pages.
Non-Final Office Action for U.S. Appl. No. 12/570,982 mailed Sep. 12, 2013, 22 pages.
Non-Final Office Action for U.S. Appl. No. 12/730,015 mailed Mar. 6, 2012, 9 pages.
Non-Final Office Action for U.S. Appl. No. 12/956,411 mailed Jan. 24, 2011, 9 pages.
Non-Final Office Action for U.S. Appl. No. 12/978,898 mailed Feb. 6, 2013, 12 pages.
Non-Final Office Action for U.S. Appl. No. 12/982,395 mailed Dec. 11, 2012, 13 pages.
Non-Final Office Action for U.S. Appl. No. 13/721,890 mailed Jan. 9, 2015, 11 pages.
Non-Final Office Action for U.S. Appl. No. 13/721,890 mailed Jun. 14, 2016, 9 pages.
Non-final Office Action for U.S. Appl. No. 13/782,909 mailed Feb. 11, 2016, 17 pages.
Non-Final Office Action for U.S. Appl. No. 13/827,676 mailed Dec. 26, 2014, 13 pages.
Non-final Office Action for U.S. Appl. No. 13/827,676 mailed Dec. 30, 2015, 23 pages.
Non-Final Office Action for U.S. Appl. No. 14/145,027 mailed Mar. 23, 2015, 13 pages.
Non-Final Office Action for U.S. Appl. No. 15/137,371 mailed May 29, 2018, 19 pages.
Non-Final Office Action for U.S. Appl. No. 15/427,746 mailed Oct. 18, 2018, 9 pages.
Non-Final Office Action for U.S. Appl. No. 16/819,258 dated Sep. 4, 2020, 6 pages.
Non-Final Office Action received for U.S. Appl. No. 15/085,166, dated Mar. 17, 2021, 11 pages.
Non-Final Office Action received for U.S. Appl. No. 16/551,962, dated Mar. 2, 2021, 16 pages.
Non-Final Office Action received for U.S. Appl. No. 16/453,509 mailed Mar. 26, 2021, 45 pages.
Non-Final Office Action received for U.S. Appl. No. 16/832,318 mailed Apr. 23, 2021, 52 pages.
Notice of Allowance and Fees(s) Due for U.S. Appl. No. 15/925,011 dated Jan. 22, 2021, 15 pages.
Notice of Allowance for U.S. Appl. No. 16/180,915 dated Dec. 11, 2020, 23 pages.
Notice of Allowance for U.S. Appl. No. 11/674,069 mailed Jul. 19, 2010, 13 pages.
Notice of Allowance for U.S. Appl. No. 12/140,015 mailed Jun. 10, 2011, 10 pages.
Notice of Allowance for U.S. Appl. No. 12/165,221 mailed Nov. 16, 2010, 6 pages.
Notice of Allowance for U.S. Appl. No. 12/189,650 mailed Aug. 13, 2010, 11 pages.
Notice of Allowance for U.S. Appl. No. 12/388,956 mailed Jun. 14, 2011, 9 pages.
Notice of Allowance for U.S. Appl. No. 12/956,411 mailed Aug. 5, 2011, 8 pages.
Notice of Allowance for U.S. Appl. No. 12/982,395 mailed Apr. 24, 2013, 9 pages.
Notice of Allowance for U.S. Appl. No. 14/181,011 dated May 15, 2019, 9 pages.
Notice of Allowance for U.S. Appl. No. 15/137,371 mailed May 2, 2019, 11 pages.
Notice of Allowance for U.S. Appl. No. 15/427,746 mailed Dec. 4, 2019, 5 pages.
Notice of Allowance for U.S. Appl. No. 15/427,746 mailed Jul. 31, 2019, 8 pages.
Notice of Allowance received for U.S. Appl. No. 14/643,468, filed Oct. 24, 2018, 22 pages.
Notice of Allowance received for U.S. Appl. No. 14/181,011, filed Feb. 13, 2019, 9 pages.
Office Action for U.S. Appl. No. 14/193,294 dated Aug. 4, 2017, 31 pages.
Office Action for U.S. Appl. No. 14/193,294 dated Mar. 22, 2018, 28 pages.
Office Action for U.S. Appl. No. 14/193,294 dated Sep. 19, 2018, 27 pages.
Office Action for U.S. Appl. No. 14/229,043 dated Feb. 27, 2019, 18 pages.
Office Action for U.S. Appl. No. 14/229,043 dated Jul. 24, 2017, 19 pages.
Office Action for U.S. Appl. No. 14/229,043 dated Sep. 5, 2019, 22 pages.
Office Action for U.S. Appl. No. 14/229,043 dated Sep. 14, 2018, 17 pages.

(56) References Cited

OTHER PUBLICATIONS

Office Action for U.S. Appl. No. 14/643,468 dated Mar. 8, 2018, 11 pages.
Office Action for U.S. Appl. No. 15/085,166 dated Dec. 27, 2018, 24 pages.
Office Action for U.S. Appl. No. 15/085,166 dated Jun. 29, 2018, 19 pages.
Office Action for U.S. Appl. No. 15/085,166 dated Mar. 3, 2020, 25 pages.
Office Action for U.S. Appl. No. 15/085,166 dated Sep. 4, 2019, 23 pages.
Office Action for U.S. Appl. No. 15/422,184 dated Aug. 27, 2019, 16 pages.
Office Action for U.S. Appl. No. 15/422,184 dated Feb. 15, 2019, 15 pages.
Office Action for U.S. Appl. No. 15/422,184 dated Jan. 14, 2020, 19 pages.
Office Action for U.S. Appl. No. 15/422,184 dated Sep. 10, 2018, 13 pages.
Office Action for U.S. Appl. No. 15/925,011 dated Jun. 27, 2019, 15 pages.
Office Action for U.S. Appl. No. 15/925,011 dated Oct. 24, 2019, 19 pages.
Office Action for U.S. Appl. No. 15/925,948 dated Jun. 25, 2019, 13 pages.
Office Action for U.S. Appl. No. 15/925,948 dated Oct. 23, 2019, 18 pages.
Office Action for U.S. Appl. No. 12/570,982 mailed Apr. 8, 2015, 9 pages.
Office Action for U.S. Appl. No. 13/782,909 mailed Jun. 25, 2015, 16 pages.
Office Action for U.S. Appl. No. 13/804,175 mailed Mar. 13, 2015, 9 pages.
Office Action for U.S. Appl. No. 14/090,113 mailed Jun. 18, 2015, 14 pages.
Office Action for U.S. Appl. No. 14/090,122 mailed Oct. 21, 2016, 12 pages.
Office Action for U.S. Appl. No. 14/090,122 mailed Sep. 11, 2015, 10 pages.
Office Action for U.S. Appl. No. 14/181,011 mailed Feb. 29, 2016, 23 pages.
Office Action for U.S. Appl. No. 14/181,011 mailed Mar. 20, 2017, 28 pages.
Office Action for U.S. Appl. No. 14/181,011 mailed Oct. 20, 2016, 28 pages.
Office Action for U.S. Appl. No. 14/181,011 mailed Sep. 12, 2017, 17 pages.
Office Action for U.S. Appl. No. 14/193,294 mailed Dec. 17, 2015, 21 pages.
Office Action for U.S. Appl. No. 14/218,326 mailed Dec. 1, 2015, 13 pages.
Opar, Alisa; "Rising drug costs prompt new uses for old pills." Nature Medicine, 1211333 (2006).
PTAB Decision on Appeal for U.S. Appl. No. 14/145,027 mailed May 31, 2018, 11 pages.
PTAB Decision on Request for Rehearing for U.S. Appl. No. 14/145,027 mailed Aug. 30, 2018, 9 pages.
Sampson, R.J., Taking Control of Health Care Costs, Best's Review—Life Health Insurance Edition, Nov. 1983, vol. 84, Issue 7, USA; Abstract only.
Siler, Sharon et al., "Safe Disposal of Unused Controlled Substances" Avalere Health 2008.
Strom, Stephanie; "Old Pills Finding New Medicine Cabinets" NY Times, May 18, 2005.
Subnotebooks, Phones, and More. St. Vincent's Gets on Track. Mobile Health Data [Online], Nov. 19, 2004. URL:http://www.awarix.com.
Supplemental Notice of Allowability received for U.S. Appl. No. 16/180,915, dated Jan. 28, 2021, 2 pages.
Supplemental Notice of Allowability received for U.S. Appl. No. 16/180,915, dated Mar. 12, 2021, 10 pages.
U.S. Notice of Allowance received for U.S. Appl. No. 16/819,258, dated Nov. 16, 2020, 8 pages, U.S.
U.S. Appl. No. 14/229,043, "Systems and Methods for Monitoring and Reporting Redemption Information at a Pharmacy for Patient Incentive Information Identified at the Time of Prescribing," Unpublished (filed Mar. 28, 2014), (Roger Pinsonneault, Inventor), (McKesson Corporation, Assignee), abandoned.
U.S. Appl. No. 15/084,034, "Prescription Provider System," Unpublished (filed Mar. 29, 2016), (Scott Genone, Inventor), (McKesson Corporation, Assignee), abandoned.
U.S. Appl. No. 15/085,166, "Alternative Therapy Identification System", Unpublished (filed Mar. 30, 2016), (Elizabeth Kaye, Inventor), (McKesson Corporation, Assignee), pending.
U.S. Appl. No. 16/832,318, "Method, Apparatus, and Computer Program Product for Estimated Prescription Costs", Unpublished (filed Mar. 27, 2020), (Stacy Hopkins, Inventor), (McKesson Corporation, Assignee), pending.
United States Patent and Trademark Office, Advisory Action for U.S. Appl. No. 15/422,184, filed Jun. 25, 2019, 4 pages, U.S.A.
United States Patent and Trademark Office, Advisory Action for U.S. Appl. No. 15/422,184, filed Mar. 26, 2020, 5 pages, U.S.A.
United States Patent and Trademark Office, Advisory Action for U.S. Appl. No. 15/925,011, filed Jan. 31, 2020, 3 pages, U.S.A.
United States Patent and Trademark Office, Advisory Action for U.S. Appl. No. 15/925,948, filed Jan. 31, 2020, 4 pages, U.S.A.
United States Patent and Trademark Office, Notice of Allowability received for U.S. Appl. No. 15/422,184, filed Nov. 16, 2020, 2 pages, U.S.A.
United States Patent and Trademark Office, Notice of Allowance received for U.S. Appl. No. 15/422,184, filed Oct. 13, 2020, 12 pages, U.S.A.
United States Patent and Trademark Office, Notice of Allowance received for U.S. Appl. No. 15/925,948, filed Nov. 5, 2020, 22 pages, U.S.A.
United States Patent and Trademark Office, Office Action for U.S. Appl. No. 15/925,011, filed Apr. 8, 2020, 17 pages, U.S.A.
United States Patent and Trademark Office, Office Action for U.S. Appl. No. 15/925,948, filed Mar. 23, 2020, 29 pages, U.S.A.
United States Patent and Trademark Office, Office Action received for U.S. Appl. No. 15/422,184, filed May 18, 2020, 31 pages, U.S.A.
United States Patent and Trademark Office, Office Action received for U.S. Appl. No. 15/925,011, filed Oct. 8, 2020, 8 pages, U.S.A.
Wisconsin Physicians Service (WPS) Insurance Corporation, "How to Read Your Explanation of Benefits Chart," Jun. 16, 2012.
www.ncoil.org/news/DrugCards2.doc dated Apr. 2002, 5 pages.
CMS Updates Drug Dashboards with Prescription Drug Pricing and Spending Data, Data, Medicare Part D, Prescription drugs (Mar. 14, 2019).
How to Estimate the Cost of a Prescription. Pam Olson, Sr. Client Services Executive, Navitus Health Solutions (Year: 2015).
United States Patent and Trademark Office, Final Office Action received for U.S. Appl. No. 16/453,509, dated Aug. 18, 2021, 16 pages, U.S.
United States Patent and Trademark Office, Non-Final Office Action received for U.S. Appl. No. 16/792,413, dated Aug. 5, 2021, 32 pages, U.S.
Scientific and Technical Information Center, Report of Information from Dialog (NPL (non-patent literature) Search Results, Abstracts only), dated Nov. 1, 2021, (Year: 2021), 9 pages.
United States Patent and Trademark Office, Advisory Action received for U.S. Appl. No. 16/453,509, dated Oct. 12, 2021, 5 pages, U.S.
United States Patent and Trademark Office, Final Office Action received for U.S. Appl. No. 16/551,962, dated Nov. 4, 2021, 32 pages, U.S.
United States Patent and Trademark Office, Final Office Action received for U.S. Appl. No. 16/832,318, dated Nov. 3, 2021, 22 pages, U.S.
Google NPL (non-patent literature) Search on "pharmacy payment benefit copay NDC database", retrieved from the Internet at <https://

(56) References Cited

OTHER PUBLICATIONS scholar.google.com/scholar?hl=en&as_sdt=3,47&g=pharmacy+payment+benefit+copay+NDC+database> on Feb. 20, 2022 at 3:02 pm, 1 page.
Google NPL (non-patent literature) Search on "pharmacy payment benefit copay NDC database", retrieved from the Internet at <https://www.google.com/search?g=pharmacy+payment+benefit+copay+ndc+database&source=int&tbs=cdr%3A1%2Ccd_min%3A1%2F1%2F2010%2 . . . > on Feb. 20, 2022 at 3:00 pm, 2 pages.
United States Patent and Trademark Office, Advisory Action received for U.S. Appl. No. 16/792,413, dated Mar. 10, 2022, 4 pages, US.
United States Patent and Trademark Office, Notice of Allowance and Fee(s) Due received for U.S. Appl. No. 17/219,526, dated Mar. 22, 2022, 11 pages, US.
United States Patent and Trademark Office, Notice of Allowance and Fee(s) Due received for U.S. Appl. No. 16/551,962, dated Mar. 16, 2022, 10 pages, US.
United States Patent and Trademark Office, Notice of Allowance and Fee(s) Due received for U.S. Appl. No. 17/092,705, dated Mar. 24, 2022, 9 pages, US.
United States Patent and Trademark Office, Notice of Allowance and Fee(s) Due received for U.S. Appl. No. 16/551,962, dated Mar. 1, 2022, 14 pages, US.
Chu, Kuan-Yu, et al., "Incremental analysis of the reengineering of an outpatient billing process: an empirical study in a public hospital", BMC Health Services Research, Jun. 13, 2013, vol. 13, No. 215, 8 pages, BioMed Central LTD, UK.
Google Patents Search (including Web Search History, Prior Art Search Printable History Generator) on "pharmacy payment benefit copay NDC database) (prescription) (code) (refills) (error code) country:US before:filing:Dec. 31, 2013", retrieved from the Internet at <https://patents.google.com/?q=pharmacy+payment+benefit+copay+NDC+database&q=prescription&q=code&q=refills&q=error+code&country=US&before=filing:20131231> retrieved on Jun. 1, 2022, 4 pages.
Google Scholar Search (including Web Search History, Prior Art Search Printable History Generator) on "pharmacy payment benefit copay NDC database prescription . . . ", retrieved from the Internet at <https://scholar.google.com/scholar?hl=en&as_sdt=0%2C47&as_ylo=2010&as_yhi=2013&q=pharmacy+payment+benefit+copay+NDC+database+pres . . . > retrieved on Jun. 1, 2022, 3 pages.
United States Patent and Trademark Office, Non-Final Office Action received for U.S. Appl. No. 16/792,413, dated May 24, 2022, 48 pages, US.
United States Patent and Trademark Office, Non-Final Office Action received for U.S. Appl. No. 16/832,318, dated Jun. 8, 2022, 17 pages, US.
United States Patent and Trademark Office, Notice of Allowance received for U.S. Appl. No. 17/092,705, dated May 31, 2022, 9 pages, US.
United States Patent and Trademark Office, Notice of Allowance received for U.S. Appl. No. 17/219,526, dated Jun. 2, 2022, 8 pages, US.
United States Patent and Trademark Office, Notice of Allowance received for U.S. Appl. No. 16/551,962, dated Jun. 8, 2022, 11 pages, US.
Dubois, Robert W., "Rx Drug Costs: List Prices Versus Net Prices and the Importance of Staying Within The Data", Health Affairs Blog, Mar. 2019, 7 pages.
Kamal, Rabah, et al., "What are the recent and forecasted trends in prescription drug spending?" Peterson—KFF Health System Tracker, Feb. 20, 2019, 19 pages, Peterson Center on Healthcare.
Cepeda, Maria Soledad, et al., "Quantification of missing prescriptions in commercial claims databases : results of a cohort study.", Pharmacoepidemiology and Drug Safety, Apr. 2017, pp. 386-392, vol. 26, Epub Jan. 25, 2017 on Wiley Online Library.
United States Patent and Trademark Office, Final Office Action received for U.S. Appl. No. 16/867,286, dated Sep. 8, 2022, 19 pages, U.S.
United States Patent and Trademark Office, Notice of Allowance received for U.S. Appl. No. 16/792,413, dated Sep. 8, 2022, 18 pages, U.S.
United States Patent and Trademark Office, Notice of Allowance received for U.S. Appl. No. 17/012,565, dated Sep. 21, 2022, 11 pages, U.S.
United States Patent and Trademark Office, Notice of Allowance received for U.S. Appl. No. 16/453,509, dated Oct. 3, 2022, 23 pages, U.S.
United States Patent and Trademark Office, Final Office Action received for U.S. Appl. No. 17/175,939, dated Oct. 5, 2022, 30 pages, U.S.
United States Patent and Trademark Office, Nonfinal Office Action received for U.S. Appl. No. 17/162,461, dated Oct. 5, 2022, 47 pages, U.S.
United States Patent and Trademark Office, Nonfinal Office Action received for U.S. Appl. No. 17/158,118, dated Oct. 7, 2022, 46 pages, U.S.
United States Patent and Trademark Office, Notice of Allowance received for U.S. Appl. No. 16/552,021, dated Oct. 20, 2022, 14 pages, U.S.
American Hospital Association, "Drug Price Proposals", dated Apr. 2019, retrieved from the Internet at <URL: https://www.aha.org/system/files/media/file/2019/04/aha-drug-policy-recommendations_2.pdf>, 8 pages.
California Health Care Foundation, "When the Price is Not Right: State Options on Prescription Drug Pricing", dated Jun. 2016, retrieved from the Internet at: <URL: https://www.chcf.org/wp-content/uploads/2017/12/PDF-WhenStateRxPricing.pdf>, 16 pages.
United States Patent and Trademark Office, Advisory Action received for U.S. Appl. No. 16/867,286, dated Dec. 6, 2022, 8 pages, US.
United States Patent and Trademark Office, Advisory Action received for U.S. Appl. No. 17/175,939, dated Dec. 22, 2022, 5 pages, US.
United States Patent and Trademark Office, Notice of Allowance received for U.S. Appl. No. 16/832,318, dated Dec. 8, 2022, 26 pages, US.
Van Nuys, Ph.D., Karen, et al., "Prescription Drug Copayment Coupon Landscape", Drug Pricing White Paper, USC Leonard D. Schaeffer Center for Health Policy and Economics, Feb. 7, 2018, retrieved from the Internet at <URL: https://healthpolicy.usc.edu/research/prescription-drug-copayment-coupon-landscape/>, 21 pages.
United States Patent and Trademark Office, Non-Final Office Action received for U.S. Appl. No. 16/867,286, dated Mar. 31, 2023, 16 pages, US.
United States Patent and Trademark Office, Non-Final Office Action received for U.S. Appl. No. 17/175,939, dated Apr. 26, 2023, 24 pages, US.
United States Patent and Trademark Office, Advisory Action received for U.S. Appl. No. 16/867,286, dated Feb. 6, 2023, 3 pages, US.
United States Patent and Trademark Office, Final Office Action received for U.S. Appl. No. 17/158,118, dated Mar. 3, 2023, 19 pages, US.
U.S. Appl. No. 16/816,460, "Adaptive System and Method for Adjudicating Claims to Reduce Member Responsibility", Unpublished (filed Mar. 12, 2020), (Michael Rea, Inventor), (RC Savings, LLC, Assignee).
United States Patent and Trademark Office, Non-Final Office Action received for U.S. Appl. No. 16/816,460, dated Mar. 3, 2023, 14 pages, U.S.
United States Patent and Trademark Office, Final Office Action received for U.S. Appl. No. 17/162,461, dated May 19, 2023, 23 pages, U.S.
United States Patent and Trademark Office, Advisory Action received for U.S. Appl. No. 17/158,118, dated May 26, 2023, 5 pages, U.S.
United States Patent and Trademark Office, Non-Final Office Action received for U.S. Appl. No. 17/674,366, dated Jun. 6, 2023, 75 pages, U.S.
United States Patent and Trademark Office, Miscellaneous Office Action, Restarting Period, received for U.S. Appl. No. 17/175,939, dated Jun. 14, 2023, 23 pages, U.S.
Viswanthan, Meera, et al., "Interventions to Improve Adherence to Self-administered Medications for Chronic Diseases in the United States," Annals of Internal Medicine, Dec. 4, 2012, retrieved from

(56) References Cited

OTHER PUBLICATIONS the Internet at <https://www.acpjournals.org/doi/full/10.7326/0003-4819-157-11-201212040-00538?rfr_dat=cr_pub++0pubmed&url_ver=Z39.88-2003&rfr_id=ori%3Arid%3Acrossref.org> on Jun. 14, 2023, 25 pages.

United States Patent and Trademark Office, Notice of Allowance received for U.S. Appl. No. 15/085,166, dated Jun. 15, 2022, 18 pages, U.S.

United States Patent and Trademark Office, Final Office Action received for U.S. Appl. No. 17/012,565, dated Jul. 25, 2022, 43 pages, U.S.

United States Patent and Trademark Office, Final Office Action received for U.S. Appl. No. 16/867,286, dated Sep. 19, 2023, 16 pages, US.

United States Patent and Trademark Office, Advisory Action received for U.S. Appl. No. 16/816,460, dated Oct. 19, 2023, 3 pages, US.

United States Patent and Trademark Office, Non-Final Office Action received for U.S. Appl. No. 17/162,461, dated Oct. 19, 2023, 25 pages, US.

United States Patent and Trademark Office, Non-Final Office Action received for U.S. Appl. No. 17/705,919, dated Aug. 17, 2023, 68 pages, US.

United States Patent and Trademark Office, Advisory Action received for U.S. Appl. No. 17/162,461, dated Aug. 24, 2023, 2 pages, US.

United States Patent and Trademark Office, Final Office Action received for U.S. Appl. No. 16/816,460, dated Aug. 10, 2023, 14 pages, U.S.

United States Patent and Trademark Office, Non-Final Office Action received for U.S. Appl. No. 17/158,118, dated Jul. 13, 2023, 18 pages, U.S.

United States Patent and Trademark Office, Final Office Action received for U.S. Appl. No. 17/674,366, dated Dec. 15, 2023, 53 pages, US.

United States Patent and Trademark Office, Final Office Action received for U.S. Appl. No. 17/158,118, dated Dec. 19, 2023, 22 pages, US.

United States Patent and Trademark Office, Non-Final Office Action received for U.S. Appl. No. 16/816,460, dated Dec. 22, 2023, 46 pages, US.

United States Patent and Trademark Office, Non-Final Office Action received for U.S. Appl. No. 17/674,366, dated Jun. 5, 2024, 54 pages, US.

United States Patent and Trademark Office, Final Office Action received for U.S. Appl. No. 17/162,461, dated Jun. 4, 2024, 38 pages, US.

United States Patent and Trademark Office, Non-Final Office Action received for U.S. Appl. No. 17/846,373, dated Apr. 5, 2024, 76 pages.

United States Patent and Trademark Office, Advisory Action received for U.S. Appl. No. 17/674,366, dated Mar. 22, 2024, 6 pages.

United States Patent and Trademark Office, Final Office Action received for U.S. Appl. No. 17/705,919, dated Feb. 28, 2024, 61 pages.

United States Patent and Trademark Office, Final Office Action received for U.S. Appl. No. 17/175,939, dated Mar. 1, 2024, 24 pages.

Bowman, Michelle, et al., "Risk Assessment of Pharmacies & Electronic Prescriptions," 2019 IEEE/ACM International Conference on Advances in Social Networks Analysis and Mining (ASONAM), Aug. 27-30, 2019, pp. 641-644, Vancouver, BC, Canada.

United States Patent and Trademark Office, Final Office Action received for U.S. Appl. No. 16/816,460, dated May 3, 2024, 22 pages, U.S.

United States Patent and Trademark Office, Non-Final Office Action received for U.S. Appl. No. 17/675,616, dated May 8, 2024, 74 pages, U.S.

United States Patent and Trademark Office, Non-Final Office Action received for U.S. Appl. No. 17/676,437, dated May 9, 2024, 73 pages, U.S.

United States Patent and Trademark Office, Examiner Interview Summary received for U.S. Appl. No. 18/098,150, dated Nov. 18, 2024, 3 pages, U.S.

United States Patent and Trademark Office, Non-Final Office Action received for U.S. Appl. No. 16/816,460, dated Nov. 21, 2024, 28 pages, US.

United States Patent and Trademark Office, Examiner Interview Summary received for U.S. Appl. No. 17/175,939, dated Dec. 3, 2024, 2 pages, US.

Gemmill, Marin, "The price elasticity of demand for prescription drugs: An exploration of demand in different settings", Doctor of Philosophy Thesis submitted to the London School of Economics and Political Science, Jan. 2008, 380 pages, UMI No. U615895, UMI Dissertation Publishing, ProQuest LLC, US.

United States Patent and Trademark Office, Advisory Action and Examiner-Initiated Interview Summary received for U.S. Appl. No. 17/705,919, dated Jun. 25, 2024, 33 pages, US.

United States Patent and Trademark Office, Examiner's Answer received for U.S. Appl. No. 16/867,286, dated Jun. 28, 2024, 9 pages, US.

United States Patent and Trademark Office, Non-Final Office Action received for U.S. Appl. No. 17/158,118, dated Jul. 18, 2024, 22 pages, US.

United States Patent and Trademark Office, Notice of Allowance received for U.S. Appl. No. 17/846,373, dated Jul. 25, 2024, 16 pages, US.

United States Patent and Trademark Office, Examiner Interview Summary received for U.S. Appl. No. 17/158,118, dated Oct. 22, 2024, 8 pages, U.S.

United States Patent and Trademark Office, Non-Final Office Action received for U.S. Appl. No. 17/501,532, dated Oct. 17, 2024, 37 pages, U.S.

United States Patent and Trademark Office, Non-Final Office Action received for U.S. Appl. No. 17/499,976, dated Oct. 1, 2024, 79 pages, U.S.

United States Patent and Trademark Office, Non-Final Office Action received for U.S. Appl. No. 17/175,939, dated Oct. 24, 2024, 17 pages, U.S.

Liu, Shiyong, et al., "Evaluating Cost-Effectiveness of Treatment Options for Diabetes Patients Using System Dynamics Modeling", Proceeding of the 2018 Winter Simulation Conference (WSC), Dec. 9-12, 2018, pp. 2577-2588, IEEE, Gothenburg, Sweden.

Tiriveedhi, V., "Impact of Precision Medicine on Drug Repositioning and Pricing: A Too Small to Thrive Crisis", Journal of Personalized Medicine, Nov. 5, 2018, 11 pages, vol. 8, No. 36, MDPI, Switzerland.

United States Patent and Trademark Office, Notice of Allowance received for U.S. Appl. No. 17/705,919, dated Sep. 3, 2024, 13 pages, USA.

United States Patent and Trademark Office, Notice of Allowance received for U.S. Appl. No. 17/675,616, dated Sep. 25, 2024, 21 pages, USA.

United States Patent and Trademark Office, Notice of Allowance received for U.S. Appl. No. 17/676,437, dated Sep. 25, 2024, 20 pages, USA.

United States Patent and Trademark Office, Advisory Action received for U.S. Appl. No. 16/816,460, dated Aug. 1, 2024, 3 pages, U.S.

United States Patent and Trademark Office, Advisory Action received for U.S. Appl. No. 17/162,461, dated Aug. 19, 2024, 2 pages, U.S.

United States Patent and Trademark Office, Non-Final Office Action received for U.S. Appl. No. 18/098,150, dated Aug. 27, 2024, 61 pages, U.S.

United States Patent and Trademark Office, Interview Summary received for U.S. Appl. No. 17/675,616, dated Aug. 15, 2024, 8 pages, U.S.

United States Patent and Trademark Office, Final Office Action received for U.S. Appl. No. 17/158,118, dated Dec. 19, 2024, 24 pages, US.

Davies, Rory, "Specialty drugs: Four options for managing costs: with specialty drug costs growing at a double-digit pace and new drugs entering the market, plan sponsors struggle to keep up. The author describes challenges plan sponsors face with some particular high-cost drugs and offers four cost-control strategies", Essay,

(56) References Cited

OTHER PUBLICATIONS

Benefits Magazine, Jun. 2017, 9 pages, vol. 54, No. 6, International Foundation of Employee Benefit Plans, US.

U.S. Appl. No. 17/491,870, "Method, Apparatus, and Computer Program Product for Using Machine Learning to Generate an Offset Amount", Unpublished (filed Oct. 1, 2021), (Jared Burdine, Inventor), (McKesson Corporation, Assignee).

U.S. Appl. No. 19/053,907, "Method, Apparatus, and Computer Program Product for Evaluating Prescription Transaction in Accordance with a Database", Unpublished (filed Feb. 14, 2025), (Phillip Draa, Inventor), (McKesson Corporation, Assignee).

U.S. Appl. No. 19/053,939, "Method, Apparatus, and Computer Program Product for Partitioning Prescription Transaction Costs in an Electronic Prescription Transaction", Unpublished (filed Feb. 14, 2025), (Phillip Draa, Inventor), (McKesson Corporation, Assignee).

United States Patent and Trademark Office, Examiner Interview Summary received for U.S. Appl. No. 17/491,870, dated Sep. 23, 2024, 3 pages, US.

United States Patent and Trademark Office, Examiner Interview Summary received for U.S. Appl. No. 16/797,277, dated Aug. 10, 2022, 7 pages, US.

United States Patent and Trademark Office, Final Office Action received for U.S. Appl. No. 17/175,939, dated Feb. 13, 2025, 16 pages, US.

United States Patent and Trademark Office, Final Office Action received for U.S. Appl. No. 17/501,532, dated Feb. 19, 2025, 11 pages, US.

United States Patent and Trademark Office, Final Office Action received for U.S. Appl. No. 18/098,150, dated Feb. 27, 2025, 25 pages, US.

United States Patent and Trademark Office, Final Office Action received for U.S. Appl. No. 17/499,976, dated Mar. 3, 2025, 16 pages, US.

United States Patent and Trademark Office, Final Office Action received for U.S. Appl. No. 16/816,460, dated Mar. 7, 2025, 27 pages, US.

United States Patent and Trademark Office, Final Office Action received for U.S. Appl. No. 16/797,277, dated Sep. 12, 2022, 23 pages, US.

United States Patent and Trademark Office, Final Office Action received for U.S. Appl. No. 17/491,870, dated Jan. 27, 2025, 16 pages, US.

United States Patent and Trademark Office, Non-Final Office Action received for U.S. Appl. No. 17/162,461, dated Feb. 10, 2025, 36 pages, US.

United States Patent and Trademark Office, Non-Final Office Action received for U.S. Appl. No. 18/138,414, dated Feb. 13, 2025, 68 pages, US.

United States Patent and Trademark Office, Non-Final Office Action received for U.S. Appl. No. 16/797,277, dated May 17, 2022, 17 pages, US.

United States Patent and Trademark Office, Non-Final Office Action received for U.S. Appl. No. 17/491,870, dated Jun. 28, 2024, 18 pages, US.

United States Patent and Trademark Office, Notice of Allowance received for U.S. Appl. No. 16/797,277, dated Dec. 21, 2022, 26 pages, US.

United States Patent and Trademark Office, Advisory Action received for U.S. Appl. No. 17/501,532, Apr. 18, 2025, 3 pages, U.S.A.

United States Patent and Trademark Office, Interview Summary received for U.S. Appl. No. 18/138,414, dated May 9, 2025, 2 pages, US.

United States Patent and Trademark Office, Notice of Allowance and Interview Summary received for U.S. Appl. No. 17/501,532, May 23, 2025, 21 pages, US.

\* cited by examiner

METHOD, APPARATUS, AND COMPUTER PROGRAM PRODUCT FOR ESTIMATING A TARGET QUANTITATIVE MEASURE BASED UPON HISTORICAL ELECTRONIC MESSAGES

TECHNOLOGICAL FIELD

Embodiments of the present disclosure relate generally to electronic messages, and more particularly, to methods, apparatuses, and computer program products for estimating a target quantitative measure based on historical electronic messages.

BACKGROUND

Electronic messages are frequently transmitted and routed amongst many components of a network. One component or entity operative in a network may transmit message requests and receive responses generated by another entity. A service provider may operate a switch to facilitate the transmission and routing of such messages and may store the messages along with any related responses received in association with the message, for subsequent retrieval and/or processing. The electronic messages may include extensive data including quantitative measures, categorical indicators, associated demographic information, and/or the like, and may be updated accordingly via the service provider and switch as directed by different components and/or systems in the network. The service provider may therefore utilize the historical electronic messages in various ways to estimate certain quantitative measures, categorical indicators, and/or the like, during various stages of processing and/or storing the electronic messages, and provide estimates to various components, entities, and/or stakeholders before real values are determined.

BRIEF SUMMARY

Methods, apparatuses, and computer program products are therefore provided for estimating a target quantitative measure to achieve a respective predictor of a binary categorical indicator, based on historical electronic messages.

An apparatus is provided, comprising at least one processor and at least one memory including computer program code, the at least one memory and the computer program code configured to, with the processor, cause the apparatus to at least access historical electronic messages associated with respective associated geographic areas, respective binary categorical indicators, and respective quantitative measures. The at least one memory and the computer program code configured to, with the processor, cause the apparatus to parse the historical electronic messages to generate historical electronic message data, and partition the historical electronic message data based on the respective geographic areas. The at least one memory and the computer program code configured to, with the processor, cause the apparatus to model the partitioned historical electronic message data based upon the respective binary categorical indicators and the respective quantitative measures. Based upon the partitioned and modelled historical electronic message data, the at least one memory and the computer program code configured to, with the processor, cause the apparatus to estimate at least one target quantitative measure to achieve a respective at least one quantitative predictor of the binary categorical indicator in the respective at least one geographic area, and adjust the at least one target quantitative measure based on a quantitative criterion of an entity.

According to certain embodiments, the quantitative criterion of the entity comprises a profit-related criterion. The at least one memory and the computer program code are further configured to cause the apparatus to at least further partition the historical electronic data based on a prescription drug identifier. The at least one target quantitative measure may comprise a price. The geographic area may be defined by a demographic indicator. The at least one quantitative predictor of the binary categorical indicator may include at least one adherence level.

The historical electronic messages may pertain to historical prescription transactions received from pharmacy computers associated with a plurality of pharmacies, wherein the respective binary categorical indicators indicate adherence or non-adherence to prescriptions, and wherein the respective quantitative measures comprise patient pay amounts. The patient pay amounts are related to a cash discount system.

According to certain embodiments, the at least one memory and the computer program code are further configured to cause the apparatus to at least receive an indication of an adjusted quantitative predictor of the binary categorical indicator, and adjust the estimated at least one target quantitative measure according to the adjusted quantitative predictor of the binary categorical indicator.

The at least one memory and the computer program code are further configured to cause the apparatus to at least receive an indication of an adjusted quantitative criteria of the entity, and adjust the estimated at least on target quantitative measure according to the adjusted quantitative criteria of the entity.

A method is also provided, including accessing historical electronic messages associated with respective associated geographic areas, respective binary categorical indicators, and respective quantitative measures. The method further includes parsing the historical electronic messages to generate historical electronic message data, and partitioning the historical electronic message data based on the respective geographic areas. The method may further include modelling the partitioned historical electronic message data based upon the respective binary categorical indicators and the respective quantitative measures. The method includes, based upon the partitioned and modelled historical electronic message data, estimating at least one target quantitative measure to achieve a respective at least one quantitative predictor of the binary categorical indicator in the respective at least one geographic area, and adjusting the at least one target quantitative measure based on a quantitative criterion of an entity.

The method may further include partitioning the historical electronic data based on a prescription drug identifier. The method may further include receiving an indication of an adjusted quantitative predictor of the binary categorical indicator, and adjust the estimated at least one target quantitative measure according to the adjusted quantitative predictor of the binary categorical indicator.

A computer program product is provided comprising at least one non-transitory computer-readable storage medium having computer-executable program code instructions stored therein, the computer-executable program code instructions comprising program code instructions to access historical electronic messages associated with respective associated geographic areas, respective binary categorical indicators, and respective quantitative measures. The computer-executable program code instructions further include program code instructions to parse the historical electronic messages to generate historical electronic message data, partition the historical electronic message data based on the respective geographic areas, and model the partitioned historical electronic message data based upon the respective binary categorical indicators and the respective quantitative measures. Based upon the partitioned and modelled historical electronic message data, the computer-executable program code instructions further include program code instructions to estimate at least one target quantitative measure to achieve a respective at least one quantitative predictor of the binary categorical indicator in the respective at least one geographic area, and adjust the at least one target quantitative measure based on a quantitative criterion of an entity.

An apparatus is also provided, with means for accessing historical electronic messages associated with respective associated geographic areas, respective binary categorical indicators, and respective quantitative measures. The apparatus further includes means for parsing the historical electronic messages to generate historical electronic message data, and means for partitioning the historical electronic message data based on the respective geographic areas. The apparatus further includes means for modelling the partitioned historical electronic message data based upon the respective binary categorical indicators and the respective quantitative measures. The apparatus further includes means for, based upon the partitioned and modelled historical electronic message data, estimating at least one target quantitative measure to achieve a respective at least one quantitative predictor of the binary categorical indicator in the respective at least one geographic area, and means for adjusting the at least one target quantitative measure based on a quantitative criterion of an entity.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the disclosure in any way. It will be appreciated that the scope of the disclosure encompasses many potential embodiments, some of which will be further described below, in addition to those here summarized.

BRIEF DESCRIPTION OF THE SEVERAL VIEWS OF THE DRAWINGS

Figure 1:
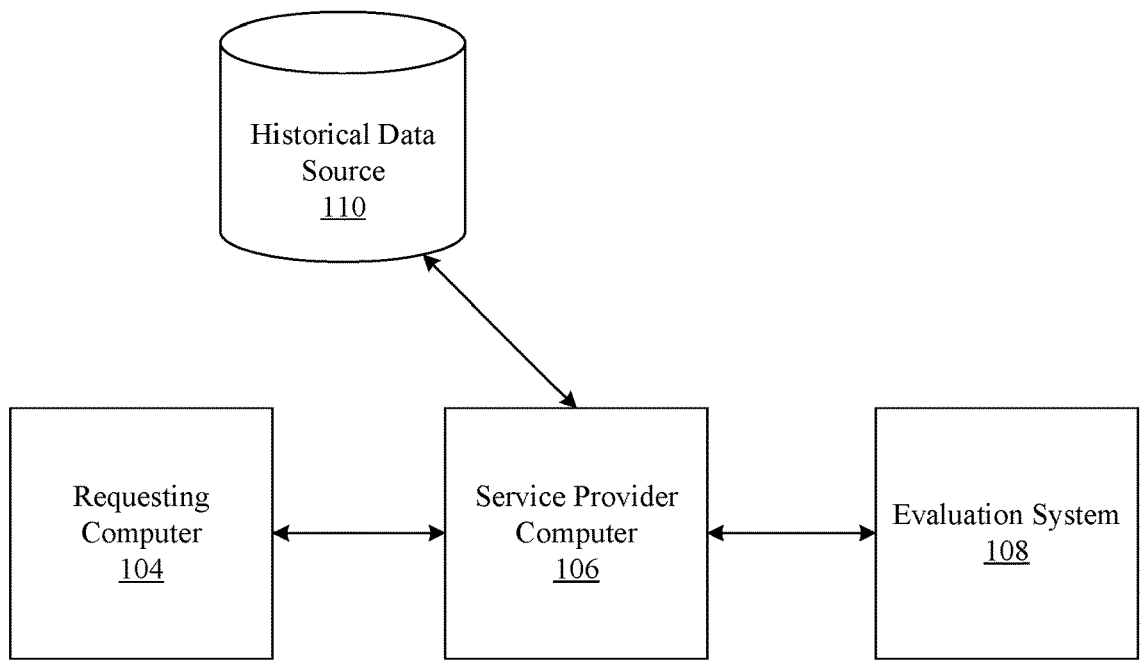
Figure 2:
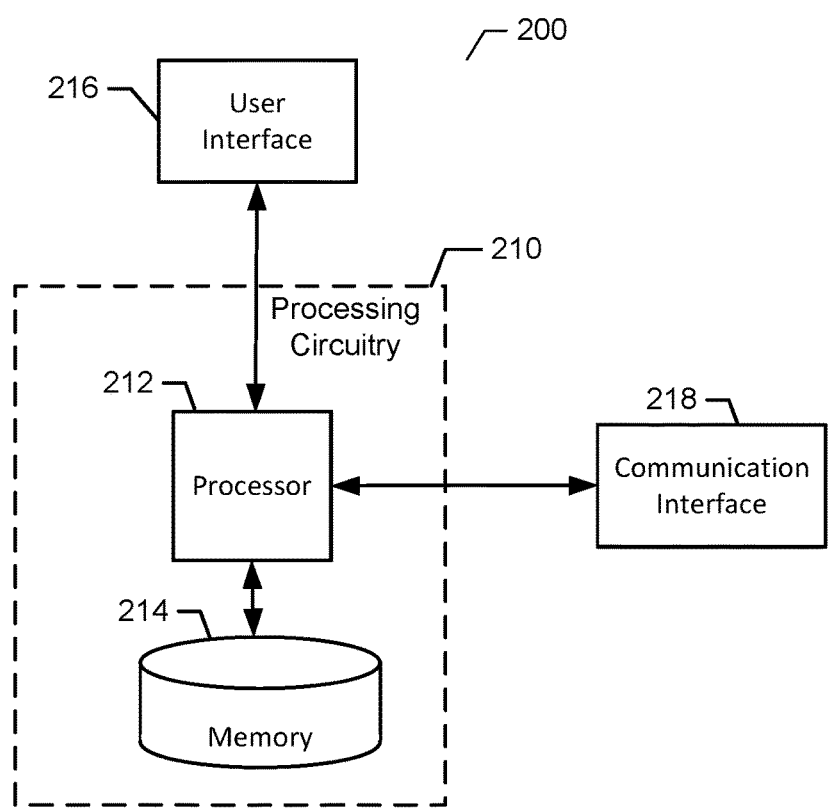
Figure 3:
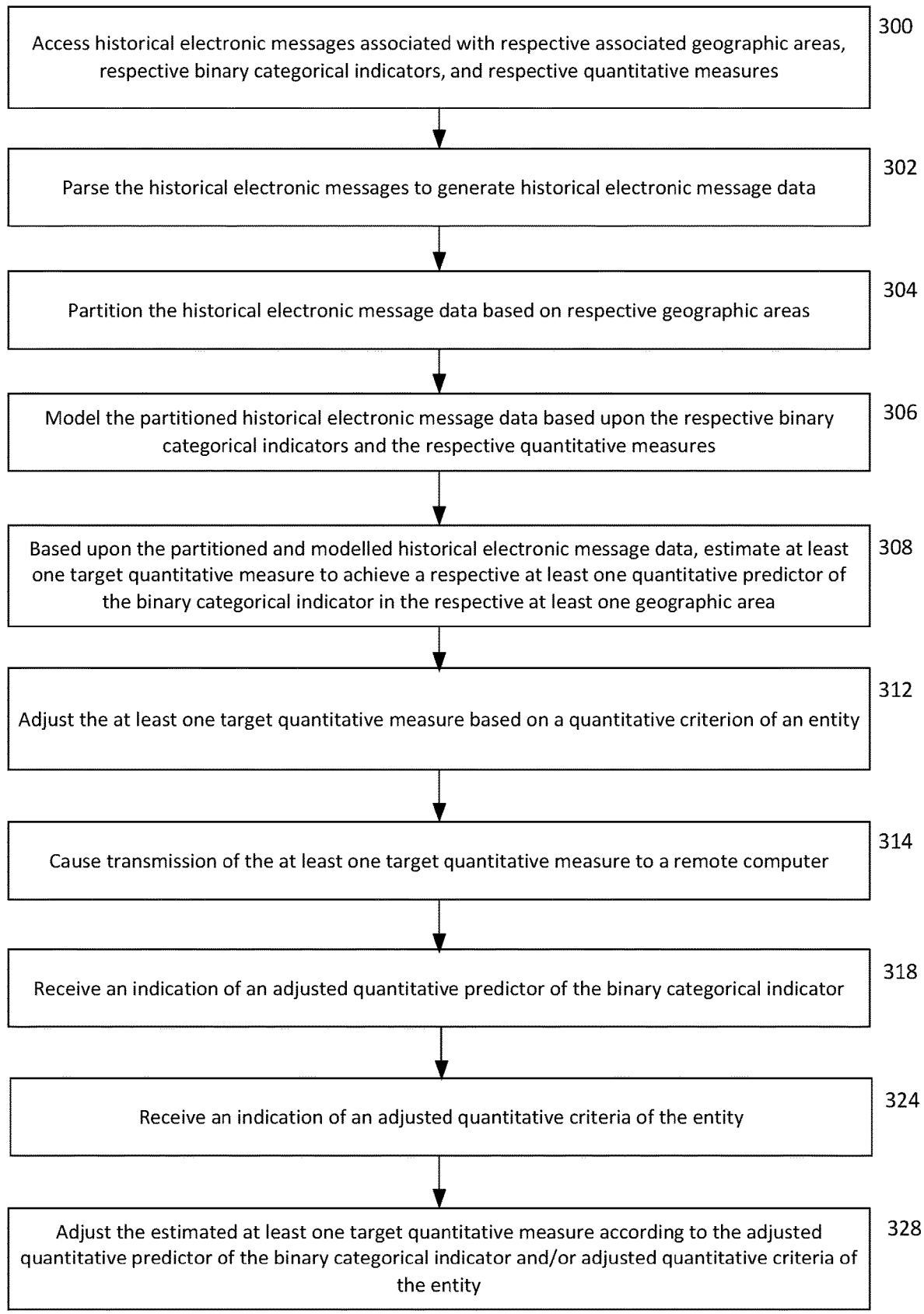
Figure 4:
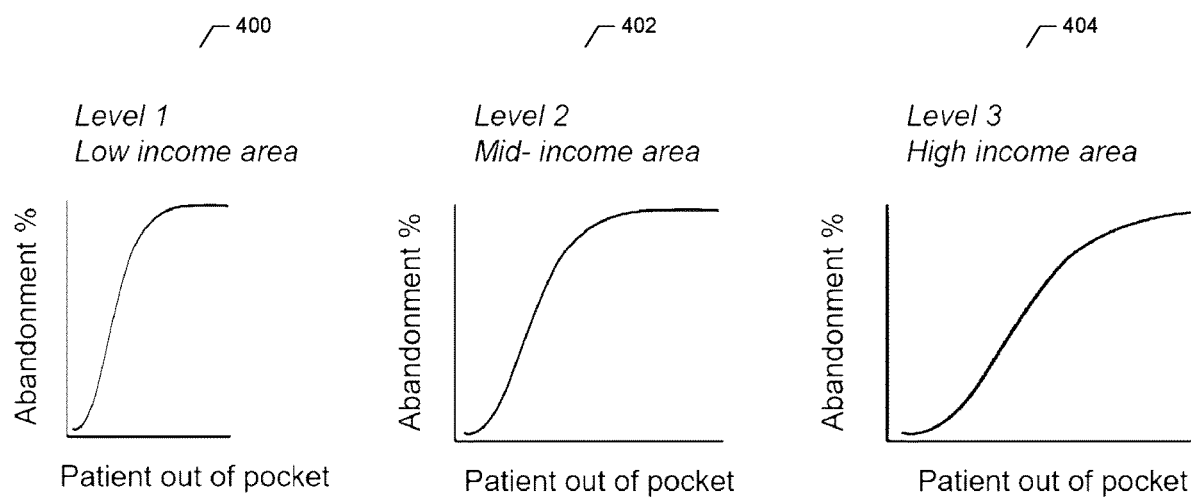

Having thus described embodiments of the invention in general terms, reference will now be made to the accompanying drawings, which are not necessarily drawn to scale, and wherein:

FIG. 1 is an example overview of a system that can be used to practice certain example embodiments described herein;

FIG. 2 is an example schematic diagram of an apparatus in accordance with certain example embodiments;

FIG. 3 is a flowchart of operations that may be performed in accordance with certain example embodiments; and FIG. 4 illustrates data modelled according to historical electronic messages in accordance with certain example embodiments.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, where a computing device is described to receive data from another computing device, it will be appreciated that the data may be received directly from the other computing device and/or may be received indirectly via one or more intermediary computing devices, such as, for example, one or more servers, relays, routers, network access points, and/or the like. Similarly, where a computing device is described herein to transmit data to another computing device, it will be appreciated that the data may be sent directly to the other computing device or may be sent to the other computing device via one or more interlinking computing devices, such as, for example, one or more servers, relays, routers, network access points, and/or the like.

FIG. 1 is an overview of a system that can be used to practice certain example embodiments. The requesting computer 104 may be any processor-driven device that facilitates the submission of electronic messages to the service provider computer 106 to request information from the service provider computer 106. Any number of requesting computers 104 may be present in a network to transmit messages to the service provider computer 106.

In certain embodiments, a requesting computer 104 may be associated with a pharmacy or pharmacy network to facilitate the filling of prescriptions, transmitting prescription claims to a service provider computer 106, and/or the like. The requesting computer 104 may additionally or alternatively be associated with a physician's office, clinic, long-term care facility, hospital, etc. Accordingly, while the exemplary requesting computer 104 may be frequently referenced herein as part of a pharmacy or pharmacy network, the requesting computer 104 may be associated with any other healthcare provider, such as a physician's office, hospital and/or other medical facility. Further, it will be appreciated that the requesting computer 104 may be implemented as a pharmacy computer, and that references herein to a "requesting computer" may be interchanged with references to a "pharmacy computer."

The requesting computer 104 may therefore facilitate the submission of electronic messages, such as prescription transactions, or prescription transactions requests, made by patients or consumers, and the communication of information associated with such messages (e.g., prescription transactions) to the service provider computer 106 to request prescription pricing information and/or the like. In certain example embodiments, the requesting computer 104 may be a point of sale device associated with a pharmacy. The execution of the computer-implemented instructions by the requesting computer 104 may form a special purpose computer or other particular machine that is operable to facilitate the submission of pharmacy transaction requests made by patients, pharmacists, and/or the like, and the communication of information associated therewith to a service provider computer 106.

The service provider computer 106 may include, but is not limited to, a processor-driven device that is configured for receiving, processing, and responding to electronic messages (e.g., prescription transactions) from the requesting computer 104. The service provider computer 106 may process such messages by routing them to various evaluation systems 108, described in further detail below. In certain embodiments, the service provider computer 106 may receive responses from evaluation systems 108 and return the response to a requesting computer 104 from which an associated transaction originated. Accordingly, the service provider computer 106 may be operable to facilitate the receipt, routing, and/or processing of healthcare transactions such as prescription transactions, prescription claims, and/or associated responses amongst various components and/or subsystems such as, but not limited to, those depicted in FIG. 1.

In certain exemplary embodiments, the service provider computer 106 may be configured as or may comprise a switch or router that evaluates, modifies, reformats, generates, and/or routes transactions such as healthcare transactions and prescription transactions. For example, the service provider computer 106 may route transactions communicated from the requesting computer 104 to an evaluation system 108 configured to return information regarding the transactions, and/or the service provider computer 106 may poll an evaluation system accordingly. In certain embodiments, the service provider computer 106 may reformat transactions into another form of transaction and modify the recipient information of the reformatted transaction before routing the reformatted transaction to another party, such as evaluation system 108. The service provider computer 106 may also optionally apply edits to at least some of the messages and/or transactions, and/or construct a separate message response for messages received via the switch.

In certain embodiments, an evaluation system 108 may be associated with a cash discount system. The evaluation system 108 may comprise a computer system that receives, adjudicates, or otherwise processes a prescription claim on behalf of the payer associated with an evaluation system 108, such as a cash discount system.

According to certain embodiments, a cash discount system may be implemented as an evaluation system 108, as illustrated in FIG. 1. Accordingly, references herein to an "evaluation system" may be interchanged with the term "cash discount system," according to certain embodiments.

Cash discount systems provide discounted prescription drugs to patients when the patient purchases a prescription at a particular pharmacy with which the cash discount system has an agreement. In some instances, a pharmacy works in agreement with a cash discount system to offer the cash price and/or discount on behalf of the cash discount system. A pharmacy may agree to cooperate with the cash discount system to compete in a price-competitive market. The pharmacy may receive a dispensing fee for dispensing the drug under the cash discount system, but may be charged administration and/or service fees that are payable to the cash discount system. Accordingly, the pharmacy's revenue for a particular transaction may include the dispensing fee, but may be reduced based on the cost of ingredients (e.g., the drug), and any applicable administration and/or fees.

In some instances, cash discount systems enable a patient to present a cash discount card and to obtain a medication at a lower cost than what would otherwise be obtainable by submitting a prescription claim to a pharmacy benefits manager (PBM), or other insurance provider, such as a commercial payer, government payer, and/or the like, for the same medication. In some instances, the patient may not have insurance coverage and a cash discount system. Cash discount systems may require fees and/or service charges payable by the pharmacy to the cash discount system, and in some cases these fees and/or services charges may increase over time, and may pose a risk to pharmacy profit margins. Pharmacies could increase the cost of prescriptions paid by patients, but in some scenarios, when prescription drug prices are further increased so as to increase or stabilize pharmacy profit margins, a patient may decline to purchase a prescription drug due to its expense, resulting in non-adherence to the prescription (e.g., abandonment of the prescription), and risking further or more advanced medical problems.

In any event, the service provider computer 106 may transmit responses from the evaluation system 108 (e.g., cash discount system) regarding the transaction information, to the requesting computer 104. For example, the service provider computer 106 may notify the requesting computer 104 of an out of pocket cost, or patient pay amount, to be paid by the patient for the prescription, such as under a cash discount system associated with the evaluation system 108.

A message or other notification may be appended to or included in the response transmitted to the requesting computer 104 indicating the cash discount system applied and patient pay amount to the patient for purchasing a drug. A patient visiting a pharmacy may then purchase the prescription drug at the offered cash price available via the cash discount system. A user of the requesting computer 104 may provide input indicating whether the transaction was completed (whether the patient purchased the prescription), and the requesting computer 104 may transmit an electronic message to the service provider computer 106. The service provider computer 106 may therefore update the transaction to reflect the completion of the transaction, therefore indicating prescription adherence. However, in some instances, the patient may choose not to purchase the drug, possibly due to the cost (e.g., patient pay amount), resulting in non-adherence to the prescription. The service provider computer 106 receives the corresponding electronic message from the requesting computer 104 and updates the transaction to indicate adherence (e.g., completion of the transaction) or non-adherence (e.g., failure to complete the transaction).

The service provider computer 106 may store the transaction, and reformat or update the transaction to reflect any of the aforementioned responses and/or electronic messages transmitted or received in association with the transaction. For example, some transactions or electronic messages may be reformatted to indicate adherence and/or non-adherence. The updated and/or reformatted transactions may be stored on the historical data source 110 as directed by the service provide computer 106 and/or requesting computer 104.

The historical data source 110 may comprise any computing device configured to provide historical information and/or data, such as but not limited to the electronic messages such as requests transmitted by requesting computer 104 in conjunction with various transactions, and optimally updated with and/or associated with responses from various evaluation systems 108. The historical data may therefore comprise historical cash pricing information of certain drugs as provided under various cash discount systems (e.g., based on responses from an evaluation system 108). The historical data may further include an indicator of the requesting computer 104 (e.g., pharmacy computer) at which the transaction was initiated and/or completed, other demographic and/or geographic information pertaining to the transaction and/or requesting computer 104 (e.g., pharmacy computer), whether or not the transaction was completed, and/or the like. The historical electronic messages may include patient data and/or may be anonymized.

According to certain embodiments, the historical data source 110 may be maintained or operated by various requesting computers 104, such as in instances in which a pharmacy tracks historical data or historical pricing of cash transactions occurring at the pharmacy. Additionally or alternatively, the historical data source 110 may be maintained or operated by the service provider computer 106, as it functions as a switch for routing and processing certain transactions submitted by various requesting computers 104.

Referring now to FIG. 2, apparatus 200 is a computing device(s) configured for implementing requesting computer 104, service provider computer 106, evaluation system 108, and/or historical data source 110, according to example embodiments.

Apparatus 200 may at least partially or wholly embody or be embodied by any of the requesting computer 104, service provider computer 106, evaluation system 108 and/or historical data source 110. Apparatus 200 may therefore implement any of the requesting computer 104, service provider computer 106, evaluation system 108, and/or historical data source 110 in accordance with some example embodiments, or may be implemented as a distributed system that includes any of the requesting computer 104, service provider computer 106, evaluation system 108, historical data source 110 and/or associated network(s).

It should be noted that the components, devices, and elements illustrated in and described with respect to FIG. 2 may not be mandatory and thus some may be omitted in certain embodiments. For example, FIG. 2 illustrates a user interface 216, as described in more detail below, which may be optional in any of the requesting computer 104 (such as when the requesting computer 104 is implemented as a service communicatively connected to a work station or other user device utilized by a pharmacist or other pharmacy employee), service provider computer 106, evaluation system 108 and/or historical data source 110. Additionally, some embodiments may include further or different components, devices, or elements beyond those illustrated in and described with respect to FIG. 2.

Continuing with FIG. 2, processing circuitry 210 may be configured to perform actions in accordance with one or more example embodiments disclosed herein. In this regard, the processing circuitry 210 may be configured to perform and/or control performance of one or more functionalities of apparatus 200 in accordance with various example embodiments. The processing circuitry 210 may be configured to perform data processing, application execution, and/or other processing and management services according to one or more example embodiments. In some embodiments apparatus 200, or a portion(s) or component(s) thereof, such as the processing circuitry 210, may be embodied as or comprise a circuit chip. The circuit chip may constitute means for performing one or more operations for providing the functionalities described herein.

In some example embodiments, the processing circuitry 210 may include a processor 212, and in some embodiments, such as that illustrated in FIG. 2, may further include memory 214. The processing circuitry 210 may be in communication with or otherwise control a user interface 216, and/or a communication interface 218. As such, the processing circuitry 210, such as that included in any of the requesting computer 104, service provider computer 106, evaluation system 108, historical data source 110, and/or apparatus 200 may be embodied as a circuit chip (e.g., an integrated circuit chip) configured (e.g., with hardware, software, or a combination of hardware and software) to perform operations described herein.

The processor 212 may be embodied in a number of different ways. For example, the processor 212 may be embodied as various processing means such as one or more of a microprocessor or other processing element, a coprocessor, a controller, or various other computing or processing devices including integrated circuits such as, for example, an ASIC (application specific integrated circuit), an FPGA (field programmable gate array), or the like. Although illustrated as a single processor, it will be appreciated that the processor 212 may comprise a plurality of processors. The plurality of processors may be in operative communication with each other and may be collectively configured to perform one or more functionalities of apparatus 200 as described herein. The plurality of processors may be embodied on a single computing device or distributed across a plurality of computing devices collectively configured to function as requesting computer 104, service provider computer 106, evaluation system 108, and/or apparatus 200. In some example embodiments, the processor 212 may be configured to execute instructions stored in the memory 214 or otherwise accessible to the processor 212. As such, whether configured by hardware or by a combination of hardware and software, the processor 212 may represent an entity (e.g., physically embodied in circuitry—in the form of processing circuitry 210) capable of performing operations according to embodiments of the present invention while configured accordingly. Thus, for example, when the processor 212 is embodied as an ASIC, FPGA, or the like, the processor 212 may be specifically configured hardware for conducting the operations described herein. Alternatively, as another example, when the processor 212 is embodied as an executor of software instructions, the instructions may specifically configure the processor 212 to perform one or more operations described herein.

In some example embodiments, the memory 214 may include one or more non-transitory memory devices such as, for example, volatile and/or non-volatile memory that may be either fixed or removable. In this regard, the memory 214 may comprise a non-transitory computer-readable storage medium. It will be appreciated that while the memory 214 is illustrated as a single memory, the memory 214 may comprise a plurality of memories. The plurality of memories may be embodied on a single computing device or may be distributed across a plurality of computing devices. The memory 214 may be configured to store information, data, applications, computer program code, instructions and/or the like for enabling apparatus 200 to carry out various functions in accordance with one or more example embodiments. For example, when apparatus 200 is implemented as service provider computer 106, memory 214 may be configured to store computer program code for performing corresponding functions thereof, as described herein according to example embodiments.

Still further, memory 214 may be configured to store routing tables, that facilitate determining the destination of communications received from a requesting computer 104, and/or evaluation system 108. Memory 214 may further include reconciliation tables for tracking the healthcare transactions and/or prescription transactions received from the requesting computer 104, and reconciling them with responses received from evaluation system 108. The memory 214 may further comprise a database, such as historical data source 110, comprising historical electronic messages. Still further, according to certain embodiments, the memory 214 may be modified as described herein, to reformat prescription claims and/or prescription transactions with additional information received, determined and/or generated according to example embodiments.

The memory 214 may be further configured to buffer input data for processing by the processor 212. Additionally or alternatively, the memory 214 may be configured to store instructions for execution by the processor 212. In some embodiments, the memory 214 may include one or more databases that may store a variety of files, content, or data sets. Among the contents of the memory 214, applications may be stored for execution by the processor 212 to carry out the functionality associated with each respective application. In some cases, the memory 214 may be in communication with one or more of the processor 212, user interface 216, and/or communication interface 218, for passing information among components of apparatus 200.

The optional user interface 216 may be in communication with the processing circuitry 210 to receive an indication of a user input at the user interface 216 and/or to provide an audible, visual, mechanical, or other output to the user. As such, the user interface 216 may include, for example, a keyboard, a mouse, a display, a touch screen display, a microphone, a speaker, and/or other input/output mechanisms. As such, in embodiments in which apparatus 200 is implemented as the requesting computer 104, the user interface 216 may, in some example embodiments, provide means for user entry of payer information (e.g., information relating to a cash discount system), details relating to the dispensing of a prescription, whether a prescription transaction was completed, and/or the like. The user interface 216 may be further configured to display or provide patient pay amounts of prescription medications, such as when apparatus 200 is implemented as a requesting computer 104. According to certain embodiments, the user interface 216 may be further configured to enable entry and/or modification of adherence targets, profit-related criteria, and/or like, as described in further detail herein. In some example embodiments, aspects of user interface 216 may be limited or the user interface 216 may not be present.

The communication interface 218 may include one or more interface mechanisms for enabling communication with other devices and/or networks. In some cases, the communication interface 218 may be any means such as a device or circuitry embodied in either hardware, or a combination of hardware and software that is configured to receive and/or transmit data from/to a network and/or any other device or module in communication with the processing circuitry 210. By way of example, the communication interface 218 may be configured to enable communication amongst any of requesting computer 104, service provider computer 106, evaluation system 108, historical data source 110 and/or apparatus 200 over a network. Accordingly, the communication interface 218 may, for example, include supporting hardware and/or software for enabling wireless and/or wireline communications via cable, digital subscriber line (DSL), universal serial bus (USB), Ethernet, or other methods.

A network, such as the network in which any of the systems of FIG. 1 or components thereof or components described herein may operate, (e.g., requesting computer 104, service provider computer 106, evaluation system 108, historical data source 110, apparatus 200, and/or the like) may include a local area network, the Internet, any other form of a network, or any combination thereof, including proprietary private and semi-private networks and public networks. The network may comprise a wired network and/or a wireless network (e.g., a cellular network, wireless local area network, wireless wide area network, some combination thereof, and/or the like).

Having now provided an example apparatus of certain example embodiments, FIG. 3 is a flowchart illustrating example operations of an apparatus 200, according to some example embodiments. The operations of FIG. 3 may be performed by apparatus 200, such as with the service provider computer 106, and/or the like.

As shown by operation 300, apparatus 200 may include means, such as processor 212, memory 214, user interface 216, communication interface 218, and/or the like, for accessing historical electronic messages associated with respective associated geographic areas, respective binary categorical indicators, and respective quantitative measures.

The service provider computer 106, such as by processor 212, may access historical electronic messages on the historical data source 110. The historical electronic messages may pertain to prescription transactions routed and stored by the service provider computer 106, and may have originated from any requesting computers 104 (e.g. pharmacy computers), such as a plurality of different requesting computers 104. According to certain embodiments, the historical electronic messages may be de-identified such that patient identifying information is not stored or known.

In operation 302, apparatus 200 may include means, such as processor 212, memory 214 and/or the like, for parsing the historical electronic messages to generate historical electronic message data. The historical electronic message data may include data regarding prior prescription transactions such as but not limited to, an identifier of the prescription drug, a quoted patient pay amount (e.g., quantitative measure), an indicator of whether the transaction was completed (e.g., binary categorical indicator indicating adherence or non-adherence), and/or any data indicative of a geographical location of the transaction.

In operation 304, apparatus 200 may include means, such as processor 212, memory 214 and/or the like, for partitioning the historical message data based on the respective geographic areas. According to certain embodiments, the geographic area may be defined by zip code, city, county, region and/or the like. In certain embodiments, addresses and/or other geographic identifiers may be determined and matched to a map database. In certain examples, the geographic areas may be defined based on demographic indicators, such as but not limited to socio-economic factors (e.g., mean income, median home value, mean home value, etc.), education level (e.g., mean education level), and/or the like. In this regard, example embodiments may contemplate a variety of data sources, such as but not limited to third party data sources for defining geographic areas, defining geographic areas based on a demographic indicator, and/or the like.

In certain embodiments, the processor 212 of example embodiments, such as apparatus 200, classify geographic areas as various levels of demographic indicators, such as but not limited to education levels, a socio-economic level or status, participation in an assistance program and/the like. For example, the geographic areas may be defined by zip code, then classified as a level 1, 2 or 3 (or any number of levels), where one end of a spectrum reflects the lowest end of a scale of demographic indicators, such as education level (e.g., no high-school degree), or the lowest end of a scale of socio-economic classes (e.g., lowest income, lowest median home value, and/or the like), and the other end of the spectrum reflects the highest end of a scale of demographic indicators, such as education level (e.g., advanced degree) or the highest end of a scale of socio-economic classes (e.g., highest income, highest median home value, and/or the like). Any number of levels or statuses may be defined on a spectrum of demographic indicators, such as education level, socio-economic classes, levels, statuses, and/or the like according to example embodiments. Any demographic indicator, characteristic, or quality of a population may be considered for describing a geographic area.

In certain example embodiments, processor 212 of apparatus 20, such as the service provider computer 106, may optionally group, or further partition the electronic message data pertaining to a particular prescription drug. In certain embodiments, the electronic message data may be first partitioned by geographic area, and then by prescription drug, or vice versa.

In any event, the processor 212 partitions the historical electronic message data based on geographic area (which may be further partitioned by prescription drug), and may therefore aggregate the geographically clustered electronic message data by a demographic indicator, such as but not limited to socio-economic level or status. In certain embodiments, if the partitioned electronic message data is not yet partitioned by prescription drug, the processor 212 of example embodiments may partition the electronic message data by prescription drug after partitioning by geography and aggregating by socio-economic level or status. Regardless of the ordering of partitioning and aggregation, historical electronic message data pertaining to a particular prescription drug 'X' may be partitioned into clusters associated with a respective socio-economic level such as a level 1, level 2, and level 3.

In operation 306, apparatus 200 may include means, such as processor 212, memory 214 and/or the like, for modeling the partitioned historical message data based on the respective binary indicators and the respective quantitative measures. In certain example embodiments, the processor 212 may model the partitioned data, grouped by socio-economic level, on an x-y plot indicative of the quantitative measure (e.g., patient pay amount) and corresponding binary indicator (e.g., adherence or non-adherence/abandonment). The processor 212 of example embodiments may therefore generate a price sensitivity model, regression analysis model and/or the like to analyze the historical electronic message data. FIG. 4 provides example curves 400, 404, and 406 for respective socio-economic levels 1, 2, and 3. The x-axis represents a quantitative measure such as a patient pay amount (e.g., patient out of pocket cost) for a particular prescription drug. The y-axis indicates the percentage of abandonment (e.g., instances in which the patient visits the pharmacy, obtains information about the prescription, but fails to complete the purchase). The processor 212 of certain example embodiments may total the number of transactions that result in abandonment, and plot the patient pay amounts and/or averages thereof associated with the abandoned transactions, as illustrated in FIG. 4.

Curve 400 representing a low-income level illustrates a steeper rise in abandonment rates as the patient pay amount of a prescription drug rises, whereas curve 404 representing a high-income level indicates a more evenly distributed abandonment rate in comparison to the quantitative measure (e.g., patient pay amount).

According to certain example embodiments and the curves 400, processor 212 of apparatus 200, such as the service provider computer 106, may predict a certain quantitative measure or patient pay amount equal to measures or amounts indicated along the x-axis, to result in an abandonment percentage as indicated by the y-axis. Processor 212 may therefore predict adherence based on an inverse of the depicted curves of FIG. 4 (not illustrated). For example, when a $100 patient out pay amount is quoted for a certain prescription drug, the historical electronic message data may indicate 95% abandonment as illustrated on a curve of FIG. 4, and 5% adherence (not illustrated). Different data models may be implemented and/or utilized for different prescription drugs and for different socio-economic levels.

In this regard, processor 212 of certain example embodiments may identify correlations within a particular geographic area(s), such as those defined based on demographic indicator such as an socio-economic level, between respective categorical indicators and respective quantitative measures as reflected in the electronic message data.

In operation 308, apparatus 200 may include means, such as processor 212, memory 214, and/or the like, for estimating at least one target quantitative measure to achieve a respective at least one quantitative predictor of the binary categorical indicator in the respective at least one geographic area, based upon the partitioned and modelled historical electronic message data. According to certain embodiments, processor 212 of the service provider computer 106 may perform operation 308 for various entities such as different pharmacies in different geographic areas. For a certain pharmacy, apparatus 200 may determine a geographic area based on an address, zip code, and/or other geographic indicator, and may determine its associated demographic indicator, such as a socio-economic level, such as according to a similar method by which demographic indicators (e.g., socio-economic levels) were determined when processing and/or partitioning data with respect to operation 304 (e.g., income level, median home prices, and/or the like).

According to certain example embodiments, each entity (e.g., pharmacy) may have an associated target adherence rate or adherence goal, which may optionally vary depending on the prescription drug. As an example, a target adherence rate may be 95% for a certain entity (e.g., pharmacy) and prescription drug. According to certain example embodiments, the processor 212 of example embodiments may default the target adherence rate for an entity (such as to 95%), but may optionally edit or adjust the target such as directed by another entity (e.g., pharmacy) as described in further detail below with respect to operation 318. The target adherence rate may therefore be considered the at least one quantitative predictor of the binary categorial indicator (e.g., adherence) that the entity (e.g., pharmacy) aims to achieve, and certain example embodiments estimate the target quantitative measure needed to achieve or fulfill the target adherence rate.

Processor 212 of the service provider computer 106 may therefore access the partitioned and/or modeled historical electronic message data for the particular geographic area (e.g., based on a demographic indicator such as socio-economic level) to determine a statistical measure of historical quantitative measures (e.g., average patient pay amount) to achieve or fulfill the target adherence rate, (e.g., quantitative predictor of the binary categorial indicator indicating adherence).

According to an example embodiment and based on an example of the historical message data, a patient visiting a pharmacy located in a certain geographic area, such as associated with a particular demographic indicator (e.g., socio-economic level 1), to obtain a prescription, may be 95% likely to purchase their prescription if the patient pay amount is $20, such that if the target adherence rate is 95%, the processor 212 estimates, at least initially, the at least one target quantitative measure as $20. In this regard, any historical electronic messages available to example embodiments such as the service provider computer 106, such as any transactions routed via a switch of the service provider computer 106, may be advantageously utilized to target patient pay amounts based on respective socio-economic levels in order to achieve certain rates of adherence.

While in certain example embodiments the target quantitative measure may be estimated as an average dollar amount accessed in the partitioned and modeled historical data, such as $20, in certain embodiments, the measure may be adjusted and/or confirmed according to a quantitative criterion (e.g., profit margin) of the entity (e.g., pharmacy). Accordingly, in operation 312, apparatus 200 may include means, such as processor 212, memory 214, and/or the like, for adjusting the at least one target quantitative measure based on a quantitative criterion of an entity.

For example, a profit margin of the entity (e.g., pharmacy) may vary according to the drug and the patient pay amount quoted or charged to the patient, which may further vary dependent upon the cash system utilized for the transaction, various administration and/or service fees, and/or other expenses or income. For instance, a pharmacy may be obligated to pay a service or administration fee, such as a card marketer administrative fee, to the cash discount system or other marketer. In some instances, an administration fee may be passed through to the patient and included in the prescription cost. The pharmacy may in some examples charge a dispensing fee which may represent income for the pharmacy in a prescription transaction. Other pharmacy income and/or expenses may be associated with the prescription transactions to calculate or estimate a pharmacy profit margin.

An entity such as a pharmacy may have quantitative criteria, such as a profit-related criterion, for transactions, such a such that their profit margin meets or exceeds a certain threshold. The pricing of the prescription drug may therefore be varied to account for the various fees and/or income and meet or exceed the target profit. A quantitative criterion (e.g., profit-related criterion) for an entity may be a target profit (e.g., minimum threshold profit) for a transaction. In certain embodiments, the quantitative criterion (e.g., profit-related criterion) may vary based on the drug and/or price range thereof. For example, the quantitative criterion (e.g., profit-related criterion, minimum threshold profit, and/or the like) for a pharmacy may be $10 for a transaction having a patient pay amount between $20 and $50, but may be higher, such as $20, for a transaction having a patient pay amount between $20 and $50. In certain embodiments, the quantitative criteria may be a percentage amount of the patient pay amount. As another example, the quantitative criteria may be calculated as an acceptable range, such as a profit margin of $8-$15 for a transaction having a patient pay amount between $20 and $50.

In any event, processor 212 of an example embodiment may adjust the estimated target quantitative measure based upon the quantitative criteria to ensure that the pharmacy satisfies (e.g., reaches or exceeds) a desired profit margin, or attempts to meet or exceed a desired profit margin. In this regard, pharmacy profit margins may be maintained or improved while attempting to improve prescription adherence. For example, the processor 212 of apparatus 200, such as the service provider computer 106, may allow a variance of 5%, or other measurable variance of the quantitative predictor (e.g., target adherence) in order to meet or exceed the quantitative criterion (e.g., profit-related criterion or minimum threshold profit) of an entity (e.g., pharmacy). In this regard, when a desired adherence and/or quantitative predictor is initially or generally configured as 90%, but the quantitative criterion would not be satisfied, example embodiments allowing for 5% variance may adjust the at least one target quantitative measure so that adherence of anywhere between 85% and 95% is achieved, to satisfy the quantitative criterion, or such that the profit margin is closer to the quantitative criterion. Many variations of the adjustment may be contemplated.

In certain embodiments, the processor 212 may confirm the estimated target quantitative measure if the estimated target quantitative measure determined in operation 308 provides that the quantitative criterion is satisfied.

In operation 314, apparatus 200 may include means, such as processor 212, memory 214, and/or the like, for causing transmission of the at least one target quantitative measure to a remote computer, such as but not limited to the requesting computer 104 (e.g., pharmacy computer). The at least one target quantitative measure may therefore be used to determine patient pay amounts for various prescription drugs. The operations 300, 302 304, 306 308, 312, and 314 may be performed on a routine basis, such as daily, weekly, and/or the like, such that the target quantitative measure (e.g., patient pay amount) may be updated based on changing economic factors relating to adherence, ingredient cost, and/or the like.

According to certain embodiments, a remote computer and/or entity associated therewith (such as a pharmacy) may utilize the estimated quantitative measure as the actual price, or patient pay amount, a patient will be charged for a prescription. For example, the patient pay amounts may be set to, or overridden by the estimated quantitate measure provided by example embodiments such as service provider computer 106. In some instances this may impact or alter pharmacy profit margins. To accommodate or make up for any change or loss in profit margins, any entity may subsidize and/or sponsor certain transactions so as to improve adherence and/or to attempt to support a target adherence level such as one indicated by the quantitative predictor. For example, an employer, or sponsor of an adherence program may subsidize certain prescriptions by payment to a pharmacy to account for a reduction in profit margin and/or the like. In this regard, the remote computer that receives the at least one quantitative target may be associated with various entities, such as a pharmacy, employer, adherence program sponsor and/or the like. Many variations may be contemplated.

In operation 318, apparatus 200 may include means, such as processor 212, memory 214, user interface 216, and/or the like, for receiving an indication of an adjusted quantitative predictor of the binary categorical indicator. Additionally or alternatively, in operation 324, apparatus 200 may include means, such as processor 212, memory 214, user interface 216, and/or the like, for receiving an indication of an adjusted quantitative criteria of the entity.

In this regard, processor 212 of apparatus 200 may modify a target adherence level and/or desired pharmacy profit margin as directed by an administrator or other user via a user interface 216. A computer application such as but not limited to a web-based application, mobile app, and/or the like may generate a user interface display configured for entry of and/or modification of the quantitative predictor of the binary categorical indicator and/or quantitative criteria of the entity.

For example, a user could adjust a target adherence level (quantitative predictor of the binary categorical indicator) from 80% to 90%. A user may further adjust desired profit margins (e.g., quantitative criteria) to a different amount, whether a dollar amount, a percentage of the transaction, and/or the like. The quantitative criteria may in certain embodiments be configured and/or adjusted for different price ranges of transactions and/or the like.

Accordingly, in operation 328, apparatus 200 may include means, such as processor 212, memory 214, and/or the like, for adjusting the estimated at least one target quantitative measure according to the adjusted quantitative predictor of the binary categorical indicator and/or adjusted quantitative criteria of the entity. In response to the adjustment of either or both quantitative predictor of the binary categorical indicator and adjusted quantitative criteria, the processor 212 of example embodiments, such as service provider computer 106, may recalculate the target quantitative measure, such as by performing any of operations 300, 302, 304, 306, 308, 312 and/or 314. In this regard an updated and/or adjusted target quantitative measure may be transmitted to the remote computer, such as requesting computer 104, pharmacy computer, and/or the like. The updated and/or adjusted target quantitative measure may therefore be returned in response to the adjustment of the quantitative predictor of the binary categorical indicator and/or quantitative criteria. In this regard, the target quantitative measures may be calibrated to the pharmacy's need.

Certain example embodiments are therefore integrated into a practical application of improving prescription adherence while balancing pharmacy profit margins. In the realm of prescription pricing and purchasing via a cash discount system, the presence of multiple entities and stakeholders may drive up pricing of such drugs and detrimentally affect adherence and/or pharmacy revenue. Example embodiments therefore utilize a service provider 106 such as one that operates a switch for adjudicating prescription claims pertaining to an array of pharmacies, geographical areas, and/or the like, to estimate target pricing such that a target adherence level can likely be achieved. The pharmacy profit margin may further be accounted for according to the quantitative criterion to support the pharmacies that serve the patients.

Certain technical improvements may also be provided according to example embodiments. Patients that do not adhere to their prescriptions often cancel a transaction at the register of their pharmacy. At the point of receiving a quoted patient pay amount, the electronic message may have been transmitted via the network such as to the service provider computer 106, evaluation system 108 (e.g., cash discount system) and/or the like, so as to obtain the patient pay amount. If the patient pay amount is too high, the patient may cancel the transaction, requiring a reversal be entered by the requesting computer 104. Reversals require additional processing, network, and memory resources to route and process messages relating to the reversals, such that example embodiments further reduce the required processing and memory resources that would otherwise be expended on the facilitation, processing and routing of reversal transactions. The reduced consumption or utilization of such resources may be realized by the requesting computer 104, service provider computer 106, and/or evaluation system 108. In certain scenarios, reversals may also result in a pharmacist having to restock the product if it has already been placed in a vial for dispersing.

It will be appreciated that the figures are each provided as examples and should not be construed to narrow the scope or spirit of the disclosure in any way. In this regard, the scope of the disclosure encompasses many potential embodiments in addition to those illustrated and described herein. Numerous other configurations may also be used to implement embodiments of the present invention.

FIG. 3 illustrates operations of a method, apparatus, and computer program product according to some example embodiments. It will be understood that each operation of the flowchart or diagrams, and combinations of operations in the flowchart or diagrams, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may comprise one or more memory devices of a computing device (for example, memory 214) storing instructions executable by a processor in the computing device (for example, by processor 212). In some example embodiments, the computer program instructions of the computer program product(s) which embody the procedures described above may be stored by memory devices of a plurality of computing devices. As will be appreciated, any such computer program product may be loaded onto a computer or other programmable apparatus (for example, apparatus 200) to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product may comprise an article of manufacture which implements the function specified in the flowchart block(s). The computer program instructions of one or more computer program products may also be loaded onto a computer or other programmable apparatus (for example, apparatus 200 and/or other apparatus) to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims.

Although specific terms are employed herein, they are used in a generic and descriptive sense only and not for purposes of limitation.

That which is claimed:

1. An apparatus comprising at least one processor and at least one memory including computer program code, the at least one memory and the computer program code configured to, with the at least one processor, cause the apparatus to at least:
    store, in a data source, prescription transactions received from pharmacy computers associated with a plurality of pharmacies, and routed to a plurality of evaluation systems;
    update the prescription transactions to include respective responses received via a communication interface from the plurality of evaluation systems, wherein the respective responses indicate adherence or non-adherence;
    receive, via a first user interface, at least one target adherence level for at least one prescription drug;
    receive, via at least a second user interface associated with a pharmacy, an indication of a variance by which to adjust the at least one target adherence level;
    apply the variance to the at least one target adherence level to generate at least one adjusted target adherence level;
    access, from the data source, the prescription transactions;
    parse the prescription transactions to generate prescription transaction data comprising at least associated geographic areas, identifiers of prescription drugs, patient pay amounts related to a cash discount system, and binary categorical indicators of adherence or non-adherence;
    partition the prescription transaction data based on the associated geographic areas and the identifiers of the prescription drugs;
    model the partitioned prescription transaction data based upon the binary categorical indicators of adherence or non-adherence and the patient pay amounts;
    based upon the partitioned and modelled prescription transaction data, estimate at least one target price of the at least one prescription drug needed to satisfy the at least one adjusted target adherence level for the at least one prescription drug in an at least one geographic area;
    with at least a processor, adjust the at least one target price of the at least one prescription drug based on a profit-related criterion of the pharmacy that sells the at least one prescription drug and based on a preliminary patient pay amount related to the cash discount system that represents an amount listed by the cash discount system to charge without discounts or rebates applied; and
    set a patient pay amount for the at least one prescription drug to the at least one adjusted target price, wherein in response to setting of the patient pay amount to the adjusted targeted price, adherence is improved, and a number of reversals of prescription claims and a corresponding consumption of computing resources are reduced, in comparison to the adherence, the number of reversals, and the consumption of the computing resources associated with an apparatus that does not adjust target prices.

2. The apparatus according to claim 1, wherein the geographic area is defined by a demographic indicator.

3. A method comprising:
    storing, in a data source, prescription transactions received from pharmacy computers associated with a plurality of pharmacies, and routed to a plurality of evaluation systems;
    updating the prescription transactions to include respective responses received via a communication interface from the plurality of evaluation systems, wherein the respective responses indicate adherence or non-adherence;
    receiving, via a first user interface, at least one target adherence level for at least one prescription drug;
    receiving, via at least a user interface associated with a pharmacy, an indication of a variance by which to adjust the at least one target adherence level;
    applying the variance to the at least one target adherence level to generate at least one adjusted target adherence level;
    accessing, from the data source, the prescription transactions;
    parsing the prescription transactions to generate prescription transaction data comprising at least geographic areas, identifiers of prescription drugs, patient pay amounts related to a cash discount system, and binary categorical indicators of adherence or non-adherence;
    partitioning the prescription transaction data based on the geographic areas;
    modelling the partitioned prescription transaction data based upon the binary categorical indicators of adherence or non-adherence and the patient pay amounts;
    based upon the partitioned and modelled prescription transaction data, estimating at least one target price of the at least one prescription drug needed to satisfy the at least one adjusted target adherence level for the at least one prescription drug in an at least one geographic area;
    with at least a processor, adjusting the at least one target price of the at least one prescription drug based on a profit-related criterion of the pharmacy that sells the at least one prescription drug and based on a preliminary patient pay amount related to the cash discount system that represents an amount listed by the cash discount system to charge without discounts or rebates applied; and
    setting a patient pay amount for the at least one prescription drug to the at least one adjusted target price, wherein in response to setting of the patient pay amount to the adjusted targeted price, adherence is improved, and a number of reversals of prescription claims and a corresponding consumption of computing resources are reduced, in comparison to the adherence, the number of reversals, and the consumption of the computing resources associated with a method that does not adjust target prices.

4. The method according to claim 3, wherein the geographic area is defined by a demographic indicator.

5. A computer program product comprising at least one non-transitory computer-readable storage medium having computer-executable program code instructions stored therein, the computer-executable program code instructions comprising program code instructions to:
    store, in a data source, prescription transactions received from pharmacy computers associated with a plurality of pharmacies, and routed to a plurality of evaluation systems;
    update the prescription transactions to include respective responses received via a communication interface from the plurality of evaluation systems, wherein the respective responses indicate adherence or non-adherence;

receive, via a first user interface, at least one target adherence level for at least one prescription drug;

receive, via at least a user interface associated with a pharmacy, an indication of a variance by which to adjust the at least one target adherence level;

apply the variance to the at least one target adherence level to generate at least one adjusted target adherence level;

access, from the data source, the prescription transactions;

parse the prescription transactions to generate prescription transaction data comprising at least associated geographic areas, identifiers of prescription drugs, patient pay amounts related to a cash discount system, and binary categorical indicators of adherence or non-adherence;

partition the prescription transaction data based on the associated geographic areas and the identifiers of the prescription drug;

model the partitioned prescription transaction data based upon the binary categorical indicators of adherence or non-adherence and the patient pay amounts;

based upon the partitioned and modelled prescription transaction data, estimate at least one target price of the at least one prescription drug to satisfy the at least one adjusted target adherence level for the at least one prescription drug in an at least one geographic area;

with at least a processor, adjust the at least one target price of the at least one prescription drug based on a profit-related criterion of the pharmacy that sells the at least one prescription drug and based on a preliminary patient pay amount related to the cash discount system that represents an amount listed by the cash discount system to charge without discounts or rebates applied; and set a patient pay amount for the at least one prescription drug to the at least one adjusted target price, wherein in response to setting of the patient pay amount to the adjusted targeted price, adherence is improved, and a number of reversals of prescription claims and a corresponding consumption of computing resources are reduced, in comparison to the adherence, the number of reversals, and the consumption of the computing resources associated with an apparatus that does not adjust target prices.

6. The apparatus according to claim 1, wherein the preliminary patient pay amount is determined based on a response from a prescription inquiry transmitted to an evaluation system associated with the cash discount system.

7. The apparatus according to claim 1, wherein the preliminary patient pay amount is determined based on a response from a prescription inquiry transmitted to an evaluation system associated with the cash discount system.

8. The apparatus according to claim 1, wherein the preliminary patient pay amount is determined based on a response from a prescription inquiry transmitted to an evaluation system associated with the cash discount system.

* * * * *